(12) United States Patent
Saiga

(10) Patent No.: US 11,805,979 B2
(45) Date of Patent: Nov. 7, 2023

(54) ENDOSCOPE CONDUIT SWITCHING DEVICE AND ENDOSCOPE

(71) Applicant: OLYMPUS CORPORATION, Tokyo (JP)

(72) Inventor: Kazuya Saiga, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 211 days.

(21) Appl. No.: 17/094,123

(22) Filed: Nov. 10, 2020

(65) Prior Publication Data

US 2021/0068780 A1 Mar. 11, 2021

Related U.S. Application Data

(63) Continuation of application No. PCT/JP2019/019985, filed on May 20, 2019.

(30) Foreign Application Priority Data

May 21, 2018 (JP) .................................. 2018-097355

(51) Int. Cl.
  *A61B 1/00* (2006.01)
  *A61B 8/12* (2006.01)
  (Continued)

(52) U.S. Cl.
  CPC ............ *A61B 1/00068* (2013.01); *A61B 1/04* (2013.01); *A61B 1/06* (2013.01); *A61B 8/12* (2013.01);
  (Continued)

(58) Field of Classification Search
  None
  See application file for complete search history.

(56) References Cited

U.S. PATENT DOCUMENTS

| 2010/0099953 A1* | 4/2010 | Suzuki ................... A61B 1/015 |
| | | 600/153 |
| 2012/0088975 A1* | 4/2012 | Morimoto .......... A61B 1/00068 |
| | | 600/159 |

(Continued)

FOREIGN PATENT DOCUMENTS

| JP | 2007-111266 A | 5/2007 |
| JP | 2009-085301 | * 4/2009 |

(Continued)

OTHER PUBLICATIONS

International Search Report dated Jul. 30, 2019 issued in PCT/JP2019/019985.

*Primary Examiner* — Shahdeep Mohammed
(74) *Attorney, Agent, or Firm* — Scully, Scott, Murphy Presser, P.C.

(57) ABSTRACT

An endoscope conduit switching device includes: an attachment to be attached to an endoscope; a movable spring bearing that is movably held by the attachment and that has a rib that is cylindrical; a movable piston that has a rib receiver groove into which the rib is inserted and that is movable to be inserted into and removed from a conduit of the endoscope; and a shaft that is movably held by the movable spring bearing; a cap that is fixed to one end of the shaft; and a first coil spring configured to bias the movable spring bearing and the cap in directions away from each other, wherein a side surface of the rib of the movable spring bearing and a side surface of the rib receiver groove of the movable piston are at least partly joined with each other.

14 Claims, 15 Drawing Sheets

(51) Int. Cl.
　　　*A61B 8/00*　　　　(2006.01)
　　　*A61B 1/04*　　　　(2006.01)
　　　*A61M 25/10*　　　(2013.01)
　　　*A61B 1/06*　　　　(2006.01)

(52) U.S. Cl.
　　　CPC ....... *A61B 8/445* (2013.01); *A61M 25/10181* (2013.11)

(56) References Cited

U.S. PATENT DOCUMENTS

| | | | |
|---|---|---|---|
| 2015/0148608 A1* | 5/2015 | Fukushima | A61B 1/00094 600/116 |
| 2015/0216393 A1* | 8/2015 | Toyoda | A61B 1/00068 600/159 |
| 2017/0143194 A1 | 5/2017 | Wolfe | |
| 2017/0290495 A1 | 10/2017 | Ando | |
| 2019/0125167 A1 | 5/2019 | Taniguchi | |
| 2019/0350441 A1* | 11/2019 | Saiga | A61B 1/00068 |
| 2019/0350446 A1* | 11/2019 | Saiga | A61B 1/00068 |

FOREIGN PATENT DOCUMENTS

| | | |
|---|---|---|
| JP | 2009-085301 A | 4/2009 |
| WO | 2017/091459 A1 | 6/2017 |
| WO | 2017/149828 A1 | 9/2017 |
| WO | 2018/003185 A1 | 1/2018 |

\* cited by examiner

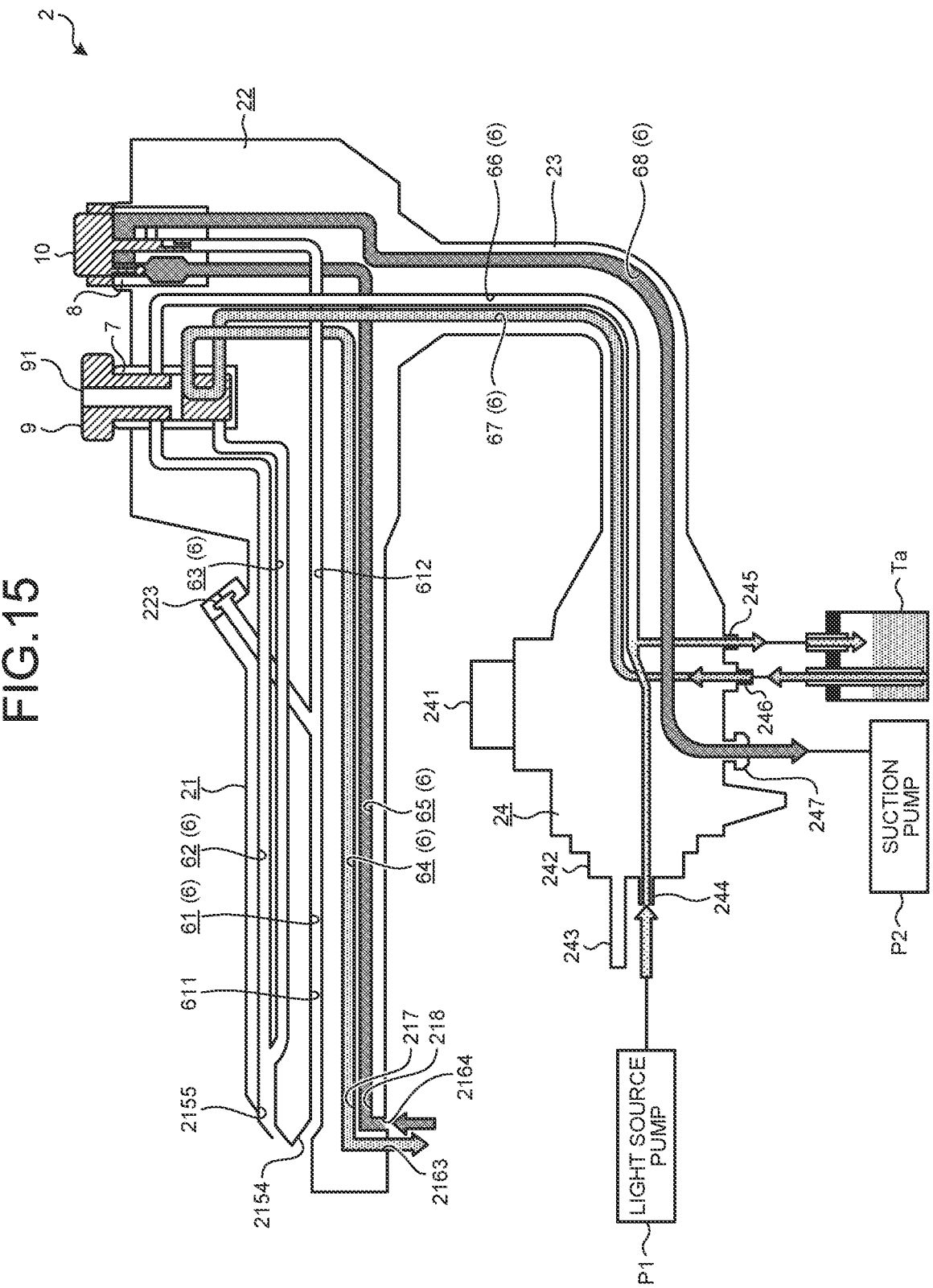

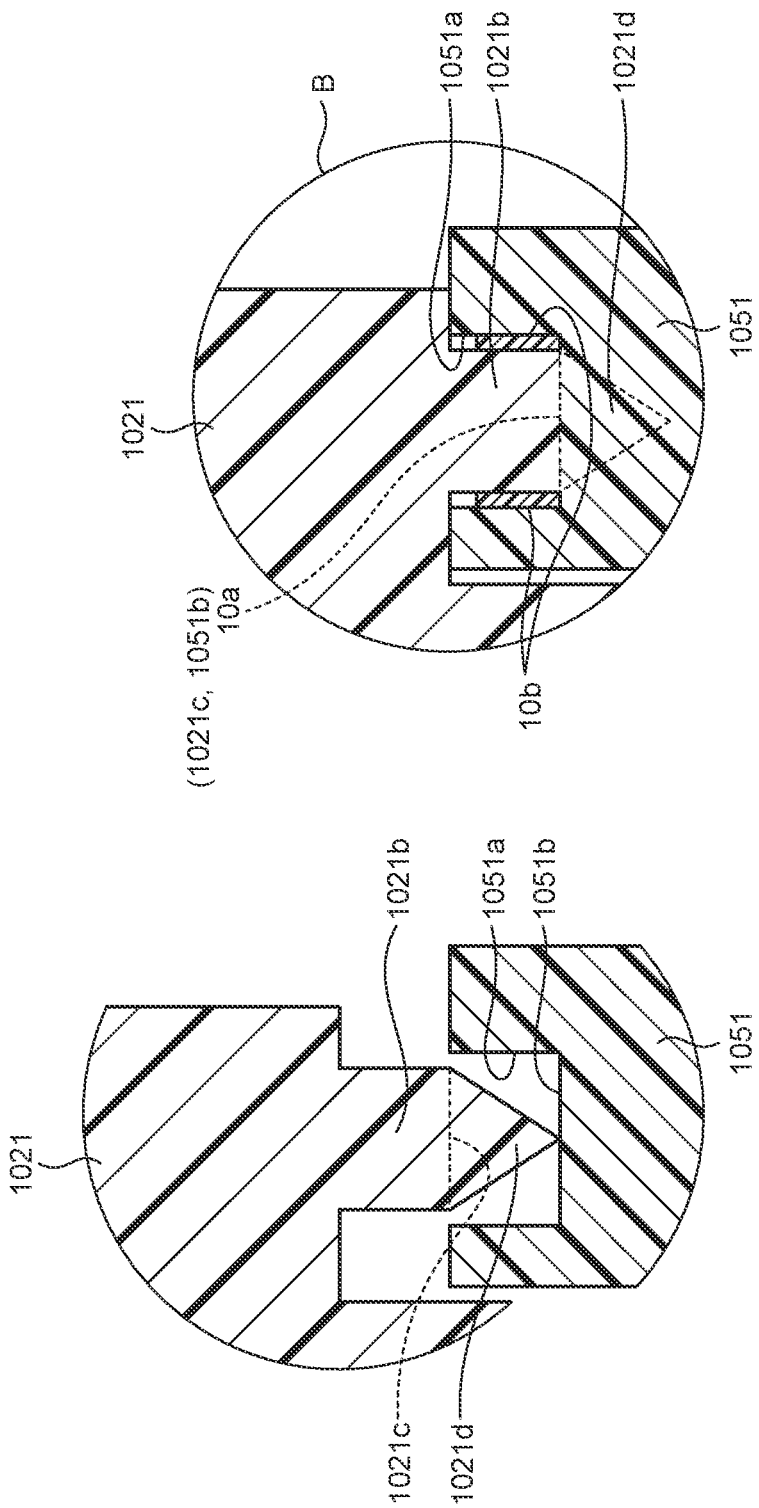

ENDOSCOPE CONDUIT SWITCHING DEVICE AND ENDOSCOPE

CROSS-REFERENCE TO RELATED APPLICATIONS

This application is a continuation of PCT International Application Ser. No. PCT/JP2019/019985, filed on May 20, 2019 which designates the United States, incorporated herein by reference, and which claims the benefit of priority from Japanese Patent Application No. 2018-097355, filed on May 21, 2018, incorporated herein by reference.

BACKGROUND

1. Technical Field

The disclosure relates to an endoscope conduit switching device an endoscope.

2. Related Art

An ultrasound endoscope whose flexible and elongated insertion portion is inserted into a subject, such as a human, and whose ultrasound transducer that is provided on a distal end side of the insertion portion transmits and receives ultrasound, thereby observing the inside of the subject, has been known.

In the ultrasound endoscope, a substance, such as a liquid, in the subject may be sucked from a taper surface that is formed at a proximal end of the insertion portion via a channel suction conduit that allows an operation portion that is provided on a proximal end side of the insertion portion and the distal end of the insertion portion to communicate. In the ultrasound endoscope, a liquid in a balloon may be sucked from a balloon filling port that is formed at the distal end of the insertion portion via a balloon suction conduit that allows the operation portion and the distal end of the insertion portion to communicate. Switching between these suction conduits is performed with an endoscope conduit switching device that is provided in the operation portion (for example, refer to Japanese Laid-open Patent Publication No. 2007-111266).

SUMMARY

In some embodiments, an endoscope conduit switching device includes: an attachment to be attached to an endoscope; a movable spring bearing that is movably held by the attachment and that has a rib that is cylindrical; a movable piston that has a rib receiver groove into which the rib is inserted and that is movable to be inserted into and removed from a conduit of the endoscope; and a shaft that is movably held by the movable spring bearing; a cap that is fixed to one end of the shaft; and a first coil spring configured to bias the movable spring bearing and the cap in directions away from each other, wherein a side surface of the rib of the movable spring bearing and a side surface of the rib receiver groove of the movable piston are at least partly joined with each other.

In some embodiments, an endoscope includes: an endoscope body including an insertion portion to be inserted into a subject and an operation portion provided on a proximal end side of the insertion portion; and the endoscope conduit switching device provided in the operation portion of the endoscope body.

In some embodiments, an endoscope conduit switching device includes: an attachment to be attached to an endoscope; a movable spring bearing that is movably held by the attachment and that has a rib that is cylindrical; a movable piston that has a rib receiver groove into which the rib is inserted and that is movable to be inserted into and removed from a conduit of the endoscope; and a second coil spring configured to bias the attachment and the movable piston in directions away from each other, wherein a side surface of the rib of the movable spring bearing and a side surface of the rib receiver groove of the movable piston are at least partly joined with each other.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 15 is a diagram illustrating a connection condition of the conduits in the case where the second-level pushing operation is performed on the air and water supply button and the suction button; and FIGS. 16A and 16B are a partial enlarged view of Area B in FIG. 7.

DETAILED DESCRIPTION

Embodiments of an endoscope disposable conduit switching device according to the disclosure will be described below with reference to the accompanying drawings. The embodiments do not limit the disclosure. In the following embodiments, a medical endoscope disposable conduit switching device will be exemplified and described, and the disclosure is applicable generally to endoscope disposable conduit switching devices including medical and industrial ones.

In the illustration of the drawings, the same or corresponding components are denoted with the same reference number. The drawings are schematic and it is necessary to note that the correlation among components in size and the ratio among the components may differ from actual ones. The drawings may contain components whose correlation in size and whose ratio differ among the drawings.

Embodiment

Figure 1:
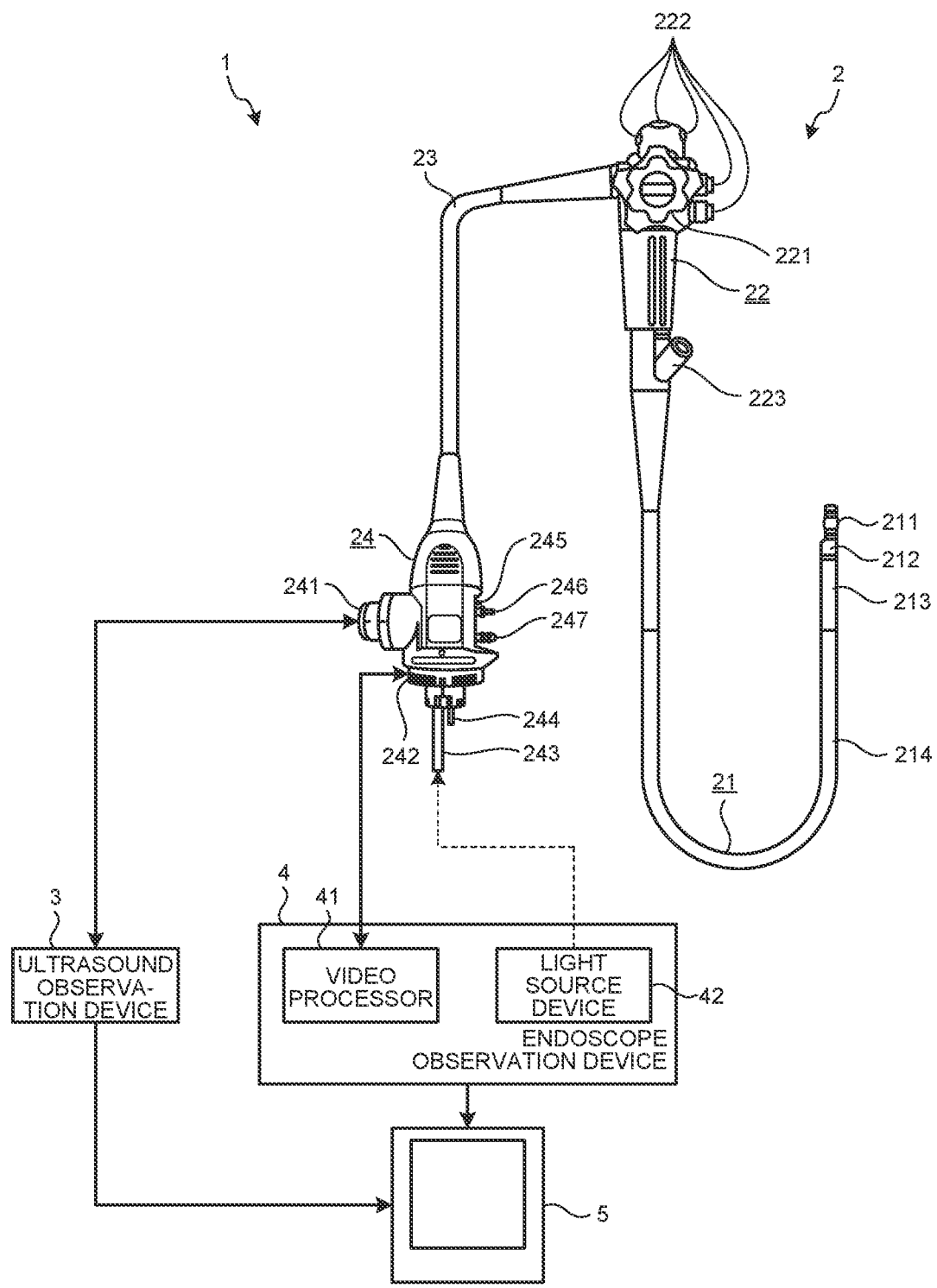
FIG. 1 is a diagram schematically illustrating an endoscope system according to an embodiment of the disclosure.

FIG. 1 is a diagram schematically illustrating an endoscope system according to an embodiment of the disclosure. An endoscope system 1 illustrated in FIG. 1 is a system that performs an in-vivo ultrasound diagnosis on a subject, such as a human, using an ultrasound endoscope. As illustrated in FIG. 1, the endoscope system 1 includes an ultrasound endoscope 2 (endoscope), an ultrasound observation device 3, an endoscope observation device 4, and a display device 5.

The ultrasound endoscope 2 has a function serving as an endoscope according to the disclosure. The ultrasound endoscope 2 is partly insertable into a subject and has a function of transmitting ultrasound pulses to a body wall in the subject, receiving ultrasound echoes that are reflected on the subject, and outputting an echo signal and a function of capturing an in-vivo image of the subject and outputting an image signal. A detailed configuration of the ultrasound endoscope 2 will be described below.

The ultrasound observation device 3 electrically connects to the ultrasound endoscope 2 via an ultrasound cable 31 and outputs a pulse signal to the ultrasound endoscope 2 via the ultrasound cable 31, and an echo signal is input to the ultrasound observation device 3 from the ultrasound endoscope 2. The ultrasound observation device 3 performs given processing on the echo signal, thereby generating an ultrasound image.

An endoscope connector 24 of the ultrasound endoscope 2 is detachably connected to the endoscope observation device 4. As illustrated in FIG. 1, the endoscope observation device 4 includes a video processor 41 and a light source device 42.

An image signal from the ultrasound endoscope 2 is input to the video processor 41 via the endoscope connector 24. The video processor 41 performs given processing on the image signal, thereby generating an endoscopic image.

The light source device 42 supplies illumination light to illuminate the inside of the subject to the ultrasound endoscope 2 via the endoscope connector 24.

The display device 5 is formed using liquid crystals or organic electro luminescence and displays the ultrasound image that is generated by the ultrasound observation device 3 and the endoscopic image that is generated by the endoscope observation device 4.

The configuration of the ultrasound endoscope 2 will be described with reference to FIGS. 1 to 5. As illustrated in FIG. 1, the ultrasound endoscope 2 includes an insertion portion 21, an operation portion 22, a universal cable 23, and the endoscope connector 24. A "distal end side" to be described below means the side of the distal end of the insertion portion 21 (the side of the distal end in the direction of insertion into the subject). A "proximal end side" to be described below means the side that separates from the distal end of the insertion portion 21.

The insertion portion 21 is a part that is inserted into the subject. As illustrated in FIG. 1, the insertion portion 21 includes an ultrasound probe 211 that is provided on the distal end side, a rigid member 212 that is continuously provided on the proximal end side of the ultrasound probe 211, a curve part 213 that is joined to the proximal end side of the rigid member 212 and that can curve, and a flexible tube 214 that is joined to the proximal end side of the curve unit 213 and is flexible.

In the insertion portion 21, the operation portion 22, the universal cable 23, and the endoscope connector 24, a light guide (not illustrated in the drawing) that transmits illumination light that is supplied from the light source device 42 and multiple signal cables (not illustrated in the drawing) that transmit the pulse signal, the echo signal, and the image signal described above are laid. A detailed configuration of the distal end side of the insertion portion 21 (the ultrasound probe 211 and the rigid member 212) will be described below.

The operation portion 22 is a unit that is joined to the proximal end side of the insertion portion 21 and that receives various operations from a doctor or the like. As illustrated in FIG. 1, the operation portion 22 includes a curve knob 221 for performing an operation of curving the curve part 213 and multiple operation members 222 for performing various operations.

In the insertion portion 21 and the operation portion 22, distal-end-side first to fifth conduits 61 to 65 (refer to FIG. 3) are provided. In the operation portion 22, an air and water supply cylinder 7 and a suction cylinder 8 (refer to FIG. 6) that communicate with the distal-end-side first to fifth conduits 61 to 65 are provided. Furthermore, an air and water supply button 9 and a suction button 10 (refer to FIG. 8) that form part of the operation members 222 and that serve as an endoscope disposable conduit switching device that switches a connection condition with respect to the distal-end-side first to fifth conduits 61 to 65 and proximal-end-side first to third conduits 66 to 68 (refer to FIG. 3) in response to an operation from a doctor, or the like, are attached to the air and water supply cylinder 7 and the suction cylinder 8, respectively. The suction button 10 corresponds to the endoscope disposable conduit switching device according to the disclosure. Detailed configurations of the conduits 6 will be described below. The connection conditions of the conduits 6 according to operations on the suction button 10 will be also described. For configurations of the air and water supply cylinder 7 and the air and water supply button 9, a known configuration (for example, refer to Japanese Laid-open Patent Publication No. 2007-111266) can be employed. Thus, description of the detailed configuration of the air and water supply cylinder 7 and the air and water supply button 9 is omitted below and, with reference to FIG. 10, etc., connection conditions of the conduits 6 according to operations on the air and water supply button 9 will be described.

The universal cable 23 is a cable that extends from the operation portion 22 and in which the aforementioned light guide (not illustrated in the drawing) and the signal cables (not illustrated in the drawing) are arranged.

The endoscope connector 24 is provided at the end of the universal cable 23. The endoscope connector 24 includes an ultrasound connector 241 to which the ultrasound cable (not illustrated in the drawing) is connected and a plug unit 242 that is inserted into the endoscope observation device 4 and that connects to the video processor 41 and the light source device 42.

The proximal-end-side first to third conduits 66 to 68 (refer to FIG. 3) that communicate with the air and water supply cylinder 7 and the suction cylinder 8 that are provided in the operation portion 22 are provided in the operation portion 22, the universal cable 23, and the endoscope connector 24.

In the plug unit 242, multiple electric contacts (not illustrated in the drawing), a light guide ferrule 243, and an air supply ferrule 244 are provided. The electric contacts are parts that electrically connect to the video processor 41 when the endoscope connector 24 is inserted into the endoscope observation device 4.

The light guide ferrule 243 is a part into which an incidence end side of the aforementioned light guide (not illustrated in the drawing) is inserted and that optically connects the light guide and the light source device 42 when the endoscope connector 24 is inserted into the endoscope observation device 4.

The air supply ferrule 244 is a part that connects to a light source pump P1 (refer to FIG. 3) provided in the light source device 42 when the endoscope connector 24 is inserted into the endoscope observation device 4.

In the endoscope connector 24, a pressure ferrule 245 and a water supply ferrule 246 to each of which an external water supply tank Ta (refer to FIG. 3) is connected and a suction ferrule 247 to which an external suction pump P2 (refer to FIG. 3) is connected are provided.

Figure 2:
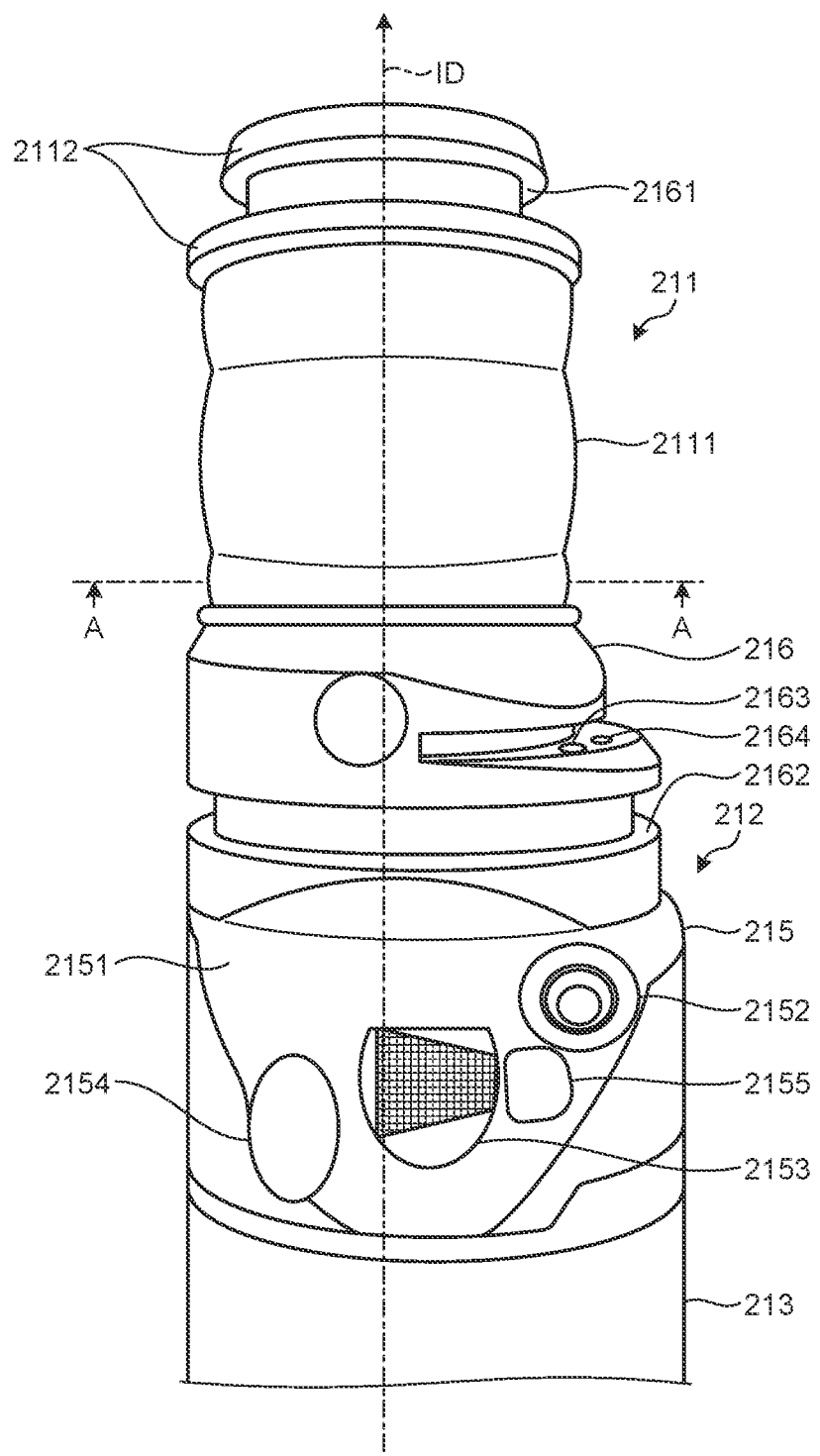
FIG. 2 is an enlarged view of a distal end side of an insertion portion.

FIG. 2 is an enlarged view of the distal end side of the insertion portion. Configurations of the ultrasound probe 211 and the rigid member 212 will be described below sequentially with reference to FIG. 2.

The ultrasound probe 211 includes a transducer unit 2111 in which a plurality of ultrasound transducers are regularly arrayed and a distal end part 2112 that is made of a metal material or a resin material. Around the outer circumference of the distal end part 2112, a balloon attachment groove 2161 for attaching a balloon (not illustrated in the drawing) that flexibly inflates and deflates and that is supplied with water is formed.

Figure 4:
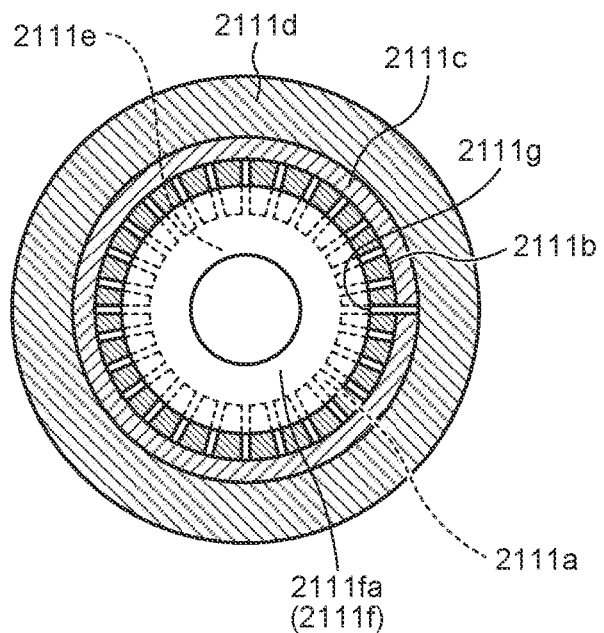
FIG. 4 is a diagram to describe a configuration of an ultrasound probe according to the embodiment of the disclosure.
Figure 5:
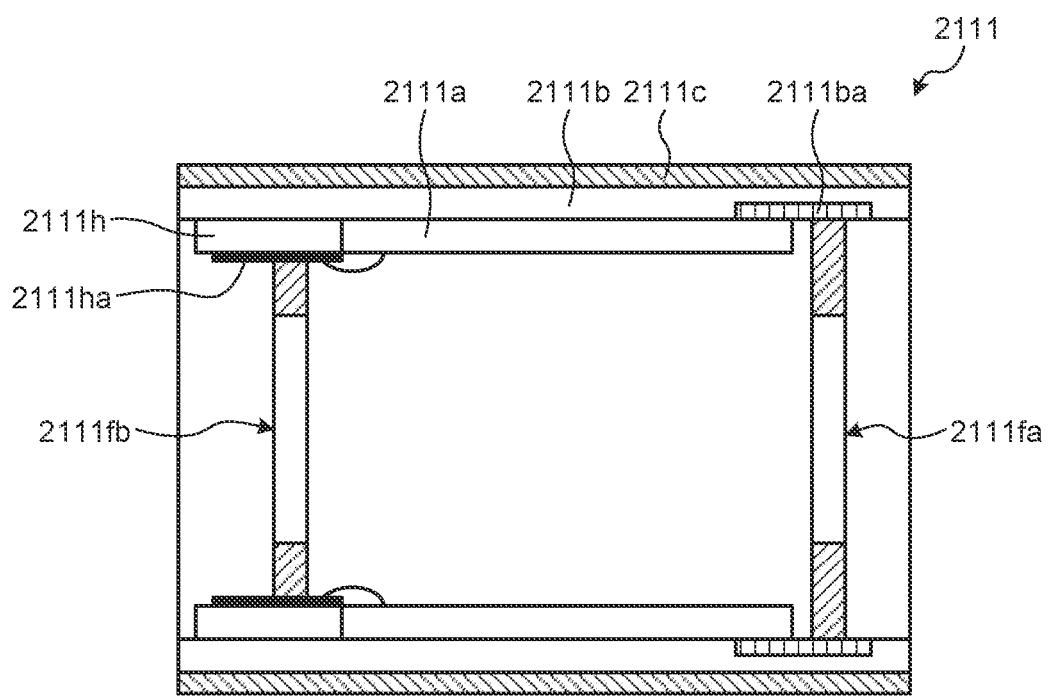
FIG. 5 is a diagram to describe the configuration of the ultrasound probe according to the embodiment of the disclosure.

FIGS. 4 and 5 are diagrams for explaining a configuration of the ultrasound probe according to the embodiment of the disclosure. FIG. 4 is a cross-sectional view corresponding to the line A-A in FIG. 2. FIG. 5 is a cross-sectional view of the transducer unit 2111 along the longitudinal direction of the insertion portion 21. As illustrated in FIGS. 4 and 5, the ultrasound probe 211 includes a plurality of piezoelectric elements 2111*a* that are cylindrical and that are arranged along the circumferential direction while being aligned in the longitudinal direction; a plurality of first acoustic matching layers 2111*b* that are provided on the inner circumferential surface side of the piezoelectric elements 2111*a*, respectively; an approximately cylindrical second acoustic matching layer 2111*c* that is provided on the side (outer surface side) opposite to the side on which the first acoustic matching layers make contact with the piezoelectric elements 2111*a*; an acoustic lens 2111*d* that is provided on the side opposite to the side on which the second acoustic matching layer makes contact with the first acoustic matching layers 2111*b*; a backing material 2111*e* that is provided on the side opposite to the side on which the piezoelectric elements 2111*a* make contact with the first acoustic matching layers 2111*b*; a structure member 2111*f* that forms a shape of a hollow disk and that is provided in order to maintain the shape of the ultrasound probe 211; a joint 2111*g* that joins the first acoustic matching layers 2111*b* and the second acoustic matching layer 2111*c*; and substrates 2111*h* (refer to FIG. 5) that are electrically connected to the piezoelectric elements 2111*a*. In the embodiment, the first acoustic matching layers 2111*b* are provided respectively for the piezoelectric element 2111*a* and the second acoustic matching layer 2111*c* and the acoustic lens 2111*d* collectively cover the piezoelectric elements 2111*a* and the first acoustic matching layers 2111*b*. Furthermore, the embodiment implements the configuration in which the backing material 2111*e* is supplied into the piezoelectric elements 2111*a*. In the ultrasound probe 211, one piezoelectric element 2111*a* may serve as a unit of output or multiple piezoelectric elements 2111*a* may serve as a unit of output.

The ultrasound probe 211 is manufactured by, after curling the sheet-shaped second acoustic matching layer 2111*c* on which the piezoelectric elements 2111*a* and the first acoustic matching layers 2111*b* are arrayed such that the piezoelectric elements 2111*a* are on the inner circumferential side and thus deforming the second acoustic matching layer 2111*c* into a cylindrical shape and arranging the structure member 2111*f*, applying an adhesive to the gap that is formed by both ends of the first acoustic matching layers 2111*b* and the second acoustic matching layer 2111*c* in the direction in which the piezoelectric elements 2111*a* are arrayed to adhere the ends, supplying an adhesive (not illustrated in the drawing) to the gap between the piezoelectric elements 2111*a* and the first acoustic matching layers 2111*b*, and supplying the backing material 2111*e* to the inner side of the piezoelectric elements 2111*a*.

The piezoelectric element 2111*a* converts an electric pulse signal into an ultrasound pulse (acoustic pulse) and applies the ultrasound pulse to a subject and converts ultrasound echoes that are reflected on the subject into an electric echo signal representing the ultrasound echoes using the change in voltage and outputs the echo signal. The piezoelectric element 2111*a* is formed using a PZT ceramic material, a PMN-PT single crystal, a PMN-PZT single crystal, a PZN-PT single crystal, a PIN-PZN-PT single crystal, or a relaxer material. The PMN-PT single crystal is an abbreviation of a solid solution of lead magnesium niobate and lead titanate. The PMN-PZT single crystal is an abbreviation of a solid solution of lead magnesium niobate and lead zirconate titanate. The PZN-PT single crystal is an abbreviation of a solid solution of lead zinc niobate and lead titanate. The PIN-PZN-PT single crystal is an abbreviation of a solid solution of lead indium niobate, lead zinc niobate, and lead titanate. The relaxer material is a generic term of a ternary system piezoelectric material obtained by adding the lead complex perovskite that is a relaxer material to lead zirconate titanate (PZT) for the purpose of increasing the piezoelectric constant and dielectric constant. The lead complex perovskite is represented by $Pb(B1,B2)O_3$ and B1 is any one of magnesium, zinc, indium, and scandium and B2 is any one of niobium, tantalum, and tungsten. These materials have superior piezoelectric effects. For this reason, even when the size is reduced, it is possible to lower the value of electric impedance and this preferable from the viewpoint of impedance matching with a film electrode that is provided on the piezoelectric element 2111*a*.

The first acoustic matching layers 2111*b* and the second acoustic matching layer 2111*c* match the acoustic impedances between the piezoelectric elements 2111*a* and a subject to be observed in order to effectively transmit sound (ultrasound) between the piezoelectric elements 2111*a* and the subject to be observed. The first acoustic matching layers 2111*b* and the second acoustic matching layer 2111*c* are made of different materials, respectively. In the embodiment, the ultrasound probe 211 is described as one including two types of acoustic matching layers (the first acoustic matching layers 2111*b* and the second acoustic matching layer 2111*c*). Alternatively, a single acoustic matching layer or three or more acoustic matching layers may be used depending on the features of the piezoelectric elements 2111*a* and the subject to be observed.

More specifically, the second acoustic matching layer 2111*c* is made of epoxy resin with silicone fillers mixed therein. It is possible to adjust the acoustic impedance by changing the compound ratio of silicone. Increasing silicone reduces the acoustic impedance. The percentage of silicone is, for example, 1 to 50% and it is preferable that the percentage be adjusted as appropriate according to the feature of the ultrasound probe 211 and the feature of the epoxy resin.

The groove that is formed between the piezoelectric elements 2111*a* and the first acoustic matching layers 2111*b* is filled with an adhesive (not illustrated in the drawing). The adhesive is an epoxy resin into which first particles whose particle diameter is of a micron order and second particles whose particle diameter is of a nano order are mixed. The first particles are, for example, silica. The second particles are, for example, alumina. For example, the first particles and the second particles of a percentage of 1 to 50% are mixed into the adhesive such that the first particles are more than the second particles. Blending the first particles reinforces the ultrasound probe 211 and blending the second particles adjusts the viscosity of the adhesive and prevents the adhesive from adhering to unnecessary parts during manufacturing.

The acoustic lens 2111*d* is formed using silicone, polymethylpentene, epoxy resin, polyetherimide, etc., and one of the faces of the acoustic lens 2111*d* is convex or concave, thus has a function of narrowing the ultrasound, and emits the ultrasound having passed through the acoustic matching layers to the outside or takes in ultrasound echoes from the outside. The acoustic lens 2111*d* may be also provided freely and a configuration without the acoustic lens 2111*d* may be employed.

The backing material 2111*e* attenuates unnecessary ultrasound vibrations that are caused by operations of the piezoelectric elements 2111*a*. The backing material 2111*e* is formed using a material whose attenuation rate is large, for example, epoxy resin into which fillers of alumina or zirconia are dispersed or rubber into which the aforementioned fillers are dispersed.

The structure member 2111*f* forms a shape of a hollow disk with an outer diameter corresponding to the diameter of the circle that the first acoustic matching layers 2111*b* form. Specifically, as illustrated in FIG. 5, the structure member 2111*f* is formed of a first structure member 2111*fa* that is provided on the side of one end in a direction (longitudinal direction) orthogonal to a plane formed by the circumferential direction of the second acoustic matching layer 2111*c* and a second structure member 2111*fb* that is provided on the side of the other end in the longitudinal direction of the second acoustic matching layer 2111*c*. The first structure member 2111*fa* forms a shape of a hollow disk with an outer diameter corresponding to the diameter of the circle that the first acoustic matching layers 2111*b* form and one of the surfaces of the first structure member 2111*fa* is covered with a conductive material, such as a copper foil. The second structure member 2111*fb* forms a shape of a hollow disk with an outer diameter corresponding to the diameter of the circle that the inner circumferential surface of the substrates 2111*h* form.

The joint 2111*g* is a joint where the sheet-like second acoustic matching layer 2111*c* on which the piezoelectric elements 2111*a* and the first acoustic matching layers 2111*b* are formed is deformed into a cylindrical shape along the direction in which the piezoelectric elements 2111*a* are arrayed and then is joined. The joint 2111*g* is made of the same material as that of the second acoustic matching layer 2111*c*. As a result, it is possible to reduce the effect of the joint 2111*g* on signals that the ultrasound probe 211 transmits and receives.

The substrates 2111*h* are electrically connected to the piezoelectric elements 2111*a* via electrodes 2111*ha* therebetween. The substrates 2111*h* are fixed to the electrodes 2111*ha* with an adhesive (not illustrated in the drawing). The adhesive is made of the same material as that of the adhesive that is supplied to the groove between the piezoelectric elements 2111*a* and the first acoustic matching layers 2111*b*. As a result, it is possible to reduce the effect of the joint 2111*g* on signals that the ultrasound probe 211 transmits and receives.

In the ultrasound probe 211 having the above-described configuration, the piezoelectric elements 2111*a* vibrate in response to an input of a pulse signal, thereby applying ultrasound to a subject to be observed via the second acoustic matching layer 2111*c* and the acoustic lens 2111*d*. During the application, in the piezoelectric elements 2111*a*, on the side opposite to the side where the first acoustic matching layers 2111*b*, the second acoustic matching layer 2111*c*, and the acoustic lens 2111*d* are arranged, the backing material 2111*e* attenuates vibrations of the piezoelectric elements 2111*a* and vibrations of the piezoelectric elements 2111*a* are not transmitted. The ultrasound that is reflected from the subject to be observed is transmitted to the piezoelectric elements 2111*a* via the first acoustic matching layers 2111*b*, the second acoustic matching layer 2111*c*, and the acoustic lens 2111*d*. The transmitted ultrasound causes the piezoelectric elements 2111*a* to vibrate and the piezoelectric elements 2111*a* convert the vibrations into an electric echo signal, and outputs the echo signal to the ultrasound observation device 3 via wiring (not illustrated in the drawing).

The rigid member 212 is a rigid member formed of a metal material or a resin material. The rigid member 212 includes a large diameter part 215 and a small diameter part 216.

The large diameter part 215 is a part to which the curve part 213 is connected and has an approximately cylindrical shape that extends along a direction ID in which the insertion portion 21 is inserted. In the large diameter part 215, a taper surface 2151 that gradually reduces the large diameter part 215 toward the distal end side is formed on an upper side. In the large diameter part 215, as illustrated in FIG. 2, an illumination hole 2152, an imaging hole 2153, an instrument channel 2154, and an air and water supply hole 2155 each of which penetrates from the proximal end of the large diameter part 215 to the taper surface 2151 are formed.

An emission end side of the above-described light guide (not illustrated in the drawing) is inserted into the illumination hole 2152. The illumination light that is supplied from the light source device 42 is applied to the inside of the subject via the illumination hole 2152.

In the imaging hole 2153, an objective optical system (not illustrated in the drawing) that focuses the light (object image) that is reflected on the inside of the subject and an imaging device (not illustrated in the drawing) that captures the object image that is focused by the objective optical system are arranged. An image signal that is captured by the imaging device is transmitted to the endoscope observation device 4 (the video processor 41) via the aforementioned signal cable (not illustrated in the drawing).

The instrument channel 2154 forms part of the distal-end-side first conduit 61.

The air and water supply hole 2155 forms part of the distal-end-side second conduit 62 and the distal-end-side third conduit 63.

The small diameter part 216 has an approximately cylindrical shape (an approximately cylindrical shape whose outer diameter dimension is smaller than that of the large diameter part 215) that extends along the direction ID in which the insertion portion 21 is inserted and the small diameter part 216 is formed integrally with the distal end of the large diameter part 215. On the proximal-end-side outer circumference of the small diameter part 216, a balloon attachment groove 2162 for attaching a balloon (not illustrated in the drawing) that flexibly inflates and deflates and that is supplied with water is formed. When the balloon is attached, the ultrasound probe 211 is inserted into the balloon from the port of the balloon (the port from which deaerated water is flown into the balloon). The port of the balloon is hooked into the balloon attachment groove 2161 and the balloon attachment groove 2162. In that state, the whole ultrasound probe 211 is covered with the balloon.

In the small diameter part 216, a balloon filling port 2163 for injecting liquid into the balloon is formed. The balloon filling port 2163 forms part of the distal-end-side fourth conduit 64.

In the small diameter part 216, a balloon suction port 2164 from which liquid, or the like, in the balloon is sucked is formed. The balloon suction port 2164 forms part of the distal-end-side fifth conduit 65.

Figure 3:
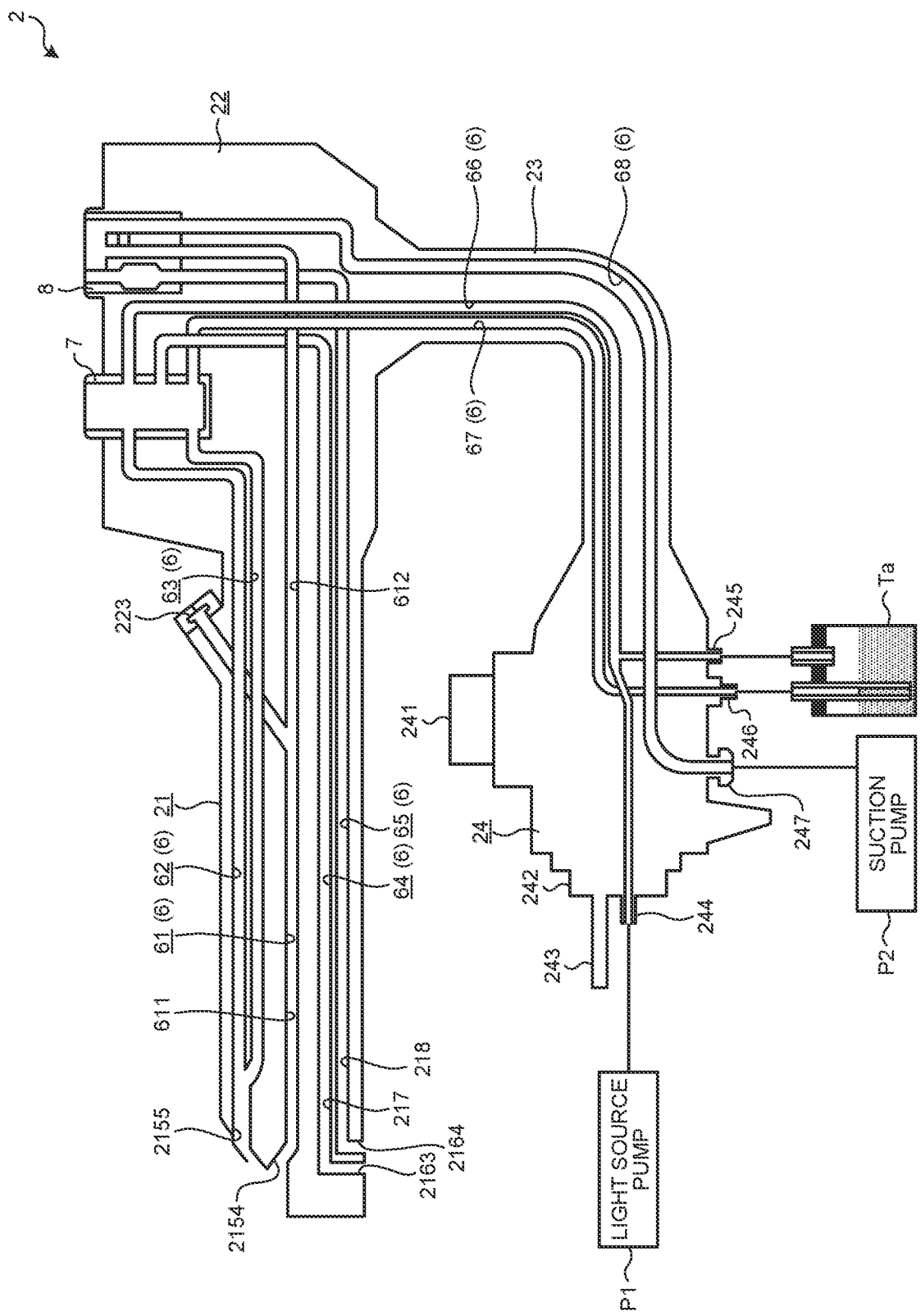
FIG. 3 is a diagram schematically illustrating a plurality of conduits that are provided in an ultrasound endoscope.

Subsequently, a configuration of the conduits 6 that are formed in the ultrasound endoscope 2 will be described with reference to FIG. 3. FIG. 3 is a diagram schematically illustrating the conduits 6 that are provided in the ultrasound endoscope 2.

As described above, the conduits 6 are formed of the distal-end-side first to fifth conduits 61 to 65 and the proximal-end-side first to third conduits 66 to 68.

The distal-end-side first conduit 61 is a conduit for allowing a treatment instrument channel (for example, a puncture needle) to protrude from the instrument channel 2154 to the outside and is a conduit for sucking liquid in the subject from the instrument channel 2154. As illustrated in FIG. 3, the distal-end-side first conduit 61 includes, a treatment instrument channel tube 611 and a suction tube 612.

The treatment instrument channel tube 611 is laid in the curve part 213 and the flexible tube 214 and an end of the treatment instrument channel tube 611 communicates with the instrument channel 2154. The treatment instrument channel tube 611 communicates with a treatment instrument channel insertion port 223 that is provided in the operation portion 22. In other words, the treatment instrument channel (for example, a puncture needle, or the like) is inserted into the treatment instrument channel tube 611 via the treatment instrument channel insertion port 223 and protrudes from the instrument channel 2154 to the outside.

The suction tube 612 is laid in the operation portion 22 and one end of the suction tube 612 communicates with the other end of the treatment instrument channel tube 611 and the other end of the suction tube 612 communicates with the suction cylinder 8.

The distal-end-side second conduit 62 is a conduit for supplying air from the air and water supply hole 2155 toward the imaging hole (not illustrated in the drawing) and is laid in the curve part 213, the flexible tube 214, and the operation portion 22 and one end of the distal-end-side second conduit 62 communicates with the air and water supply hole 2155 and the other end of the distal-end-side second conduit 62 communicates with the air and water supply cylinder 7.

The distal-end-side third conduit 63 is a conduit for supplying water from the air and water supply hole 2155 toward the imaging hole (not illustrated in the drawing) and is laid in the curve part 213, the flexible tube 214, and the operation portion 22 and one end of the distal-end-side third conduit 63 communicates with the air and water supply hole 2155 and the other end of the distal-end-side third conduit 63 communicates with the air and water supply cylinder 7.

The distal-end-side fourth conduit 64 is a conduit for supplying water into the balloon (not illustrated in the drawing) from a water supply hole 217 and is laid in the curve part 213, the flexible tube 214, and the operation portion 22 and one end of the distal-end-side fourth conduit 64 communicates with the balloon filling port 2163 and the other end of the distal-end-side fourth conduit 64 communicates with the air and water supply cylinder 7.

The distal-end-side fifth conduit 65 is a conduit for sucking water in the balloon (not illustrated in the drawing) from a suction hole 218 and is laid in the curve part 213, the flexible tube 214, and the operation portion 22 and one end of the distal-end-side fifth conduit 65 communicates with the balloon suction port 2164 and the other end of the distal-end-side fifth conduit 65 communicates with the suction cylinder 8.

The proximal-end-side first conduit 66 is a conduit that circulates the air that is ejected from the light source pump P1 to the air and water supply cylinder 7 and the water supply tank Ta and is laid in the operation portion 22, the universal cable 23, and the endoscope connector 24. One ends of the two parts into which the proximal-end-side first conduit 66 bifurcates in the endoscope connector 24 communicate respectively with the air supply ferrule 244 and the pressure ferrule 245 and the other end of the proximal-end-side first conduit 66 communicates with the air and water supply cylinder 7.

The proximal-end-side second conduit 67 is a conduit that circulates the water that is ejected from the water supply tank Ta to the air and water supply cylinder 7 and is laid in the operation portion 22, the universal cable 23, and the endoscope connector 24. One end of the proximal-end-side second conduit 67 communicates with the water supply ferrule 246 and the other end of the proximal-end-side second conduit 67 communicates with the air and water supply cylinder 7.

The proximal-end-side third conduit 68 is a conduit for sucking liquid in the suction cylinder 8 and is laid in the operation portion 22, the universal cable 23, and the endoscope connector 24. One end of the proximal-end-side third conduit 68 communicates with the suction ferrule 247 and the other end of the proximal-end-side third conduit 68 communicates with the suction cylinder 8.

Figure 6:
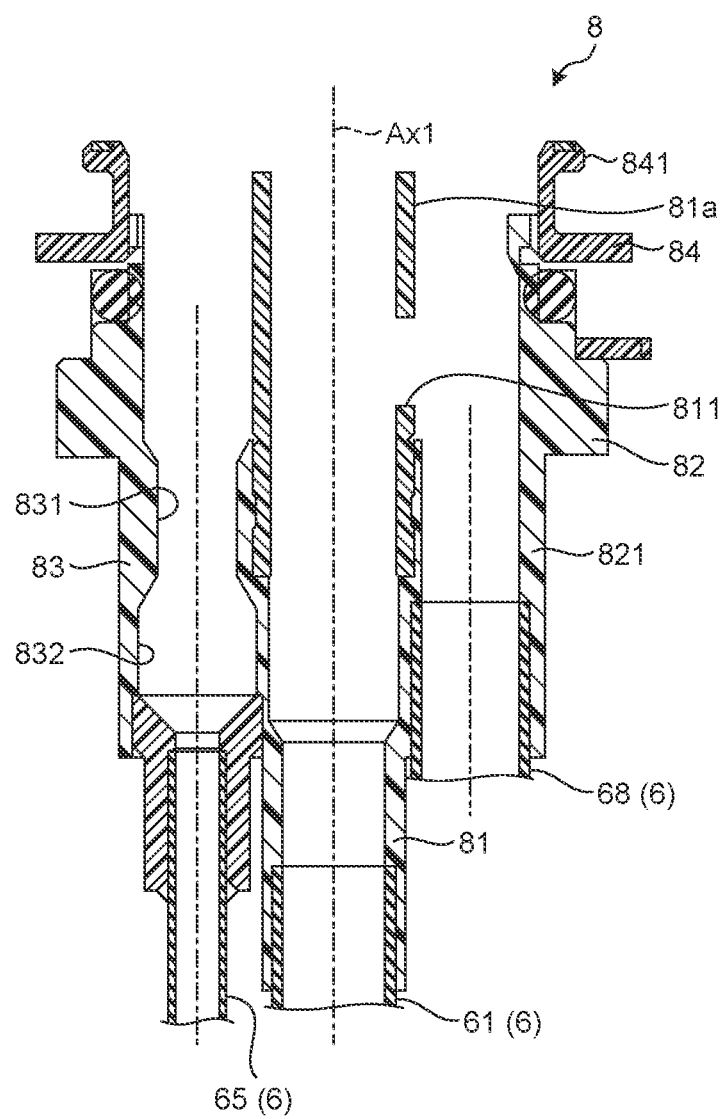
FIG. 6 is a cross-sectional view illustrating a configuration of a suction cylinder.

A configuration of the suction cylinder 8 will be described with reference to FIG. 6. FIG. 6 is a cross-sectional view illustrating the configuration of the suction cylinder. The suction cylinder 8 forms a shape of a cylinder whose center axis is a center axis Ax extending vertically in FIG. 6. As illustrated in FIG. 6, the suction cylinder 8 includes a first communication conduit 81, a cylindrical part 82 covering the outer circumference of the first communication conduit 81, and a third communication conduit 83 that extends in a position separating from the center axis Ax1 in a direction along the center axis Ax1.

A first communication pipe 81*a* with an inner diameter that allows a shaft 103 of the suction button 10 to be described below to slidably fit into the first communication pipe 81*a* is connected to the top end part of the first communication conduit 81 coaxially with and integrally with the first communication conduit 81. In the first communication pipe 81*a*, a communication hole 811 that communicates with the cylindrical part 82 is formed. As illustrated in FIG. 6, the other end of the distal-end-side first conduit 61 is connected to the bottom end part of the first communication conduit 81 via a ferrule, or the like.

As illustrated in FIG. 6, a second communication conduit 821 is formed in part of the bottom surface of the cylindrical part 82 and the other end of the proximal-end-side third conduit 68 is connected to the second communication conduit 821. As illustrated in FIG. 6, a ferrule 84 for attaching the suction button 10 is fixed to the top end of the cylindrical part 82.

The third communication conduit 83 includes, from above, a small diameter part 831 and a large diameter part 832. As illustrated in FIG. 6, the other end of the distal-end-side fifth conduit 65 is connected to the third communication conduit 83 via a ferrule, or the like, interposed in between.

The ferrule 84 has a cylindrical shape and is fixed to the outer circumference of the cylindrical part 82 by, for example, threading. While kept being fixed to the outer circumferential surface of the cylindrical part 82, the ferrule 84 protrudes from the inside of the operation portion 22 to the outside. As illustrated in FIG. 6, on the outer circumference of the ferrule 84, an engagement protrusion 841 that has a circular shape extending around the whole outer circumference and that projects from the top end of the outer circumferential surface to a side on which the engagement protrusion 841 separates from the center axis Ax1 is provided.

Figure 7:
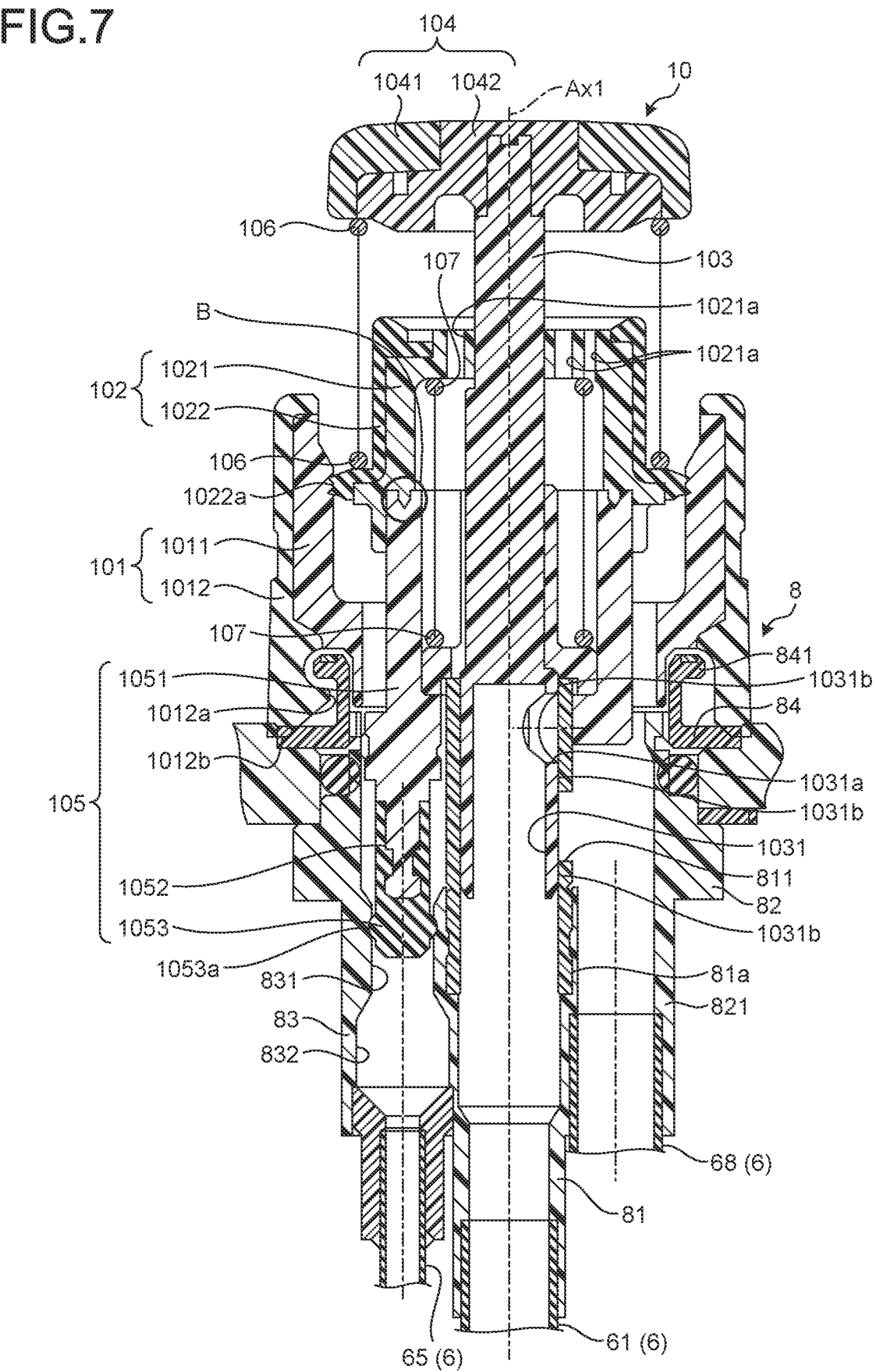
FIG. 7 is a cross-sectional view illustrating a suction button being mounted on a suction cylinder.
Figure 8:
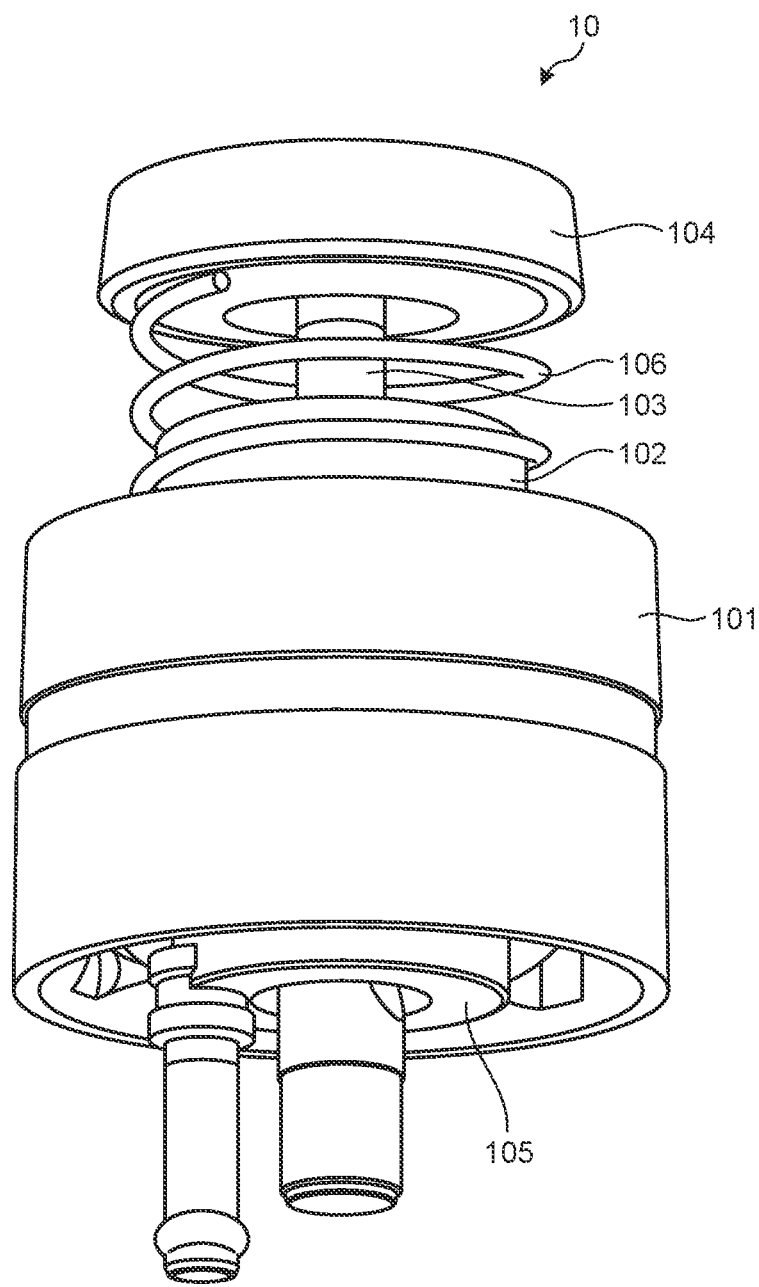
FIG. 8 is a perspective view of a configuration of the suction button.
Figure 9:
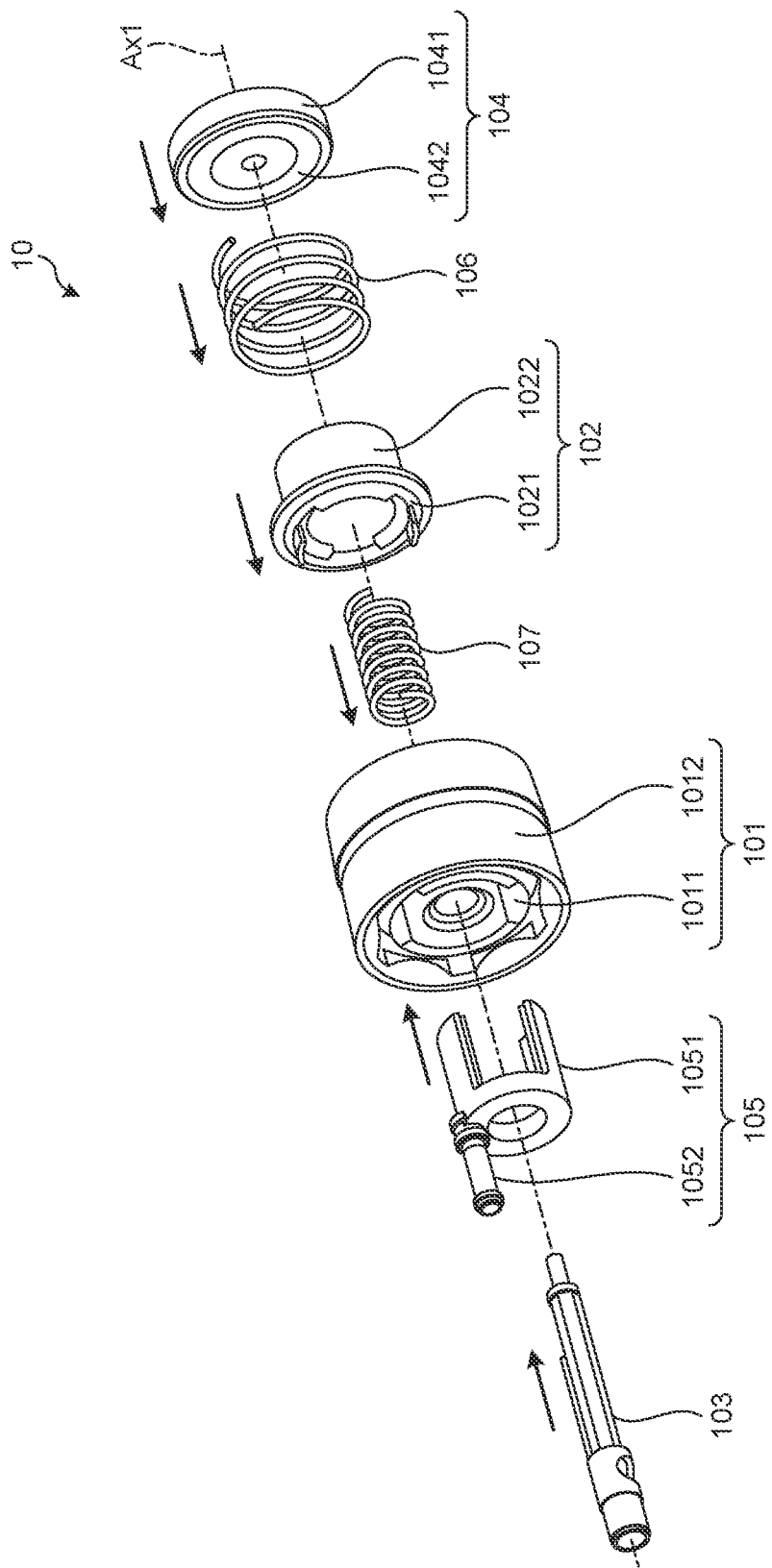
FIG. 9 is an exploded perspective view of the suction button.

A configuration of the suction button 10 will be described with reference to FIGS. 7 to 9. FIG. 7 is a cross-sectional view illustrating the suction button being mounted on the suction cylinder. Specifically, FIG. 7 is a cross-sectional view illustrating the suction button 10 being mounted on the ferrule 84 (the suction cylinder 8). In other words, the lower side in FIG. 7 illustrates the distal end side in the direction in which the suction button 10 is mounted on the ferrule 84. FIG. 8 is a perspective view illustrating the configuration of the suction button. FIG. 9 is a perspective exploded view of the suction button.

The suction button 10 includes an attachment 101 that is attached to the ferrule 84 (the suction cylinder 8), a movable spring bearing 102 that is held movably by the attachment 101, the shaft 103 that is movably held by the movable spring bearing 102, a cap 104 that is fixed to one end of the shaft 103, a movable piston 105 that is fixed to the movable spring bearing 102, a first coil spring 106 that biases the movable spring bearing 102 and the cap 104 in directions such that the movable spring bearing 102 and the cap 104 separate from each other, and a second coil spring 107 that biases the attachment 101 and the movable spring bearing 102 (the movable piston) in directions such that the attachment 101 and the movable spring bearing 102 separate from each other. The suction button 10 is detachable from the ultrasound endoscope 2. As a result, when a diagnosis is made again after a diagnosis is made, the used suction button 10 is detached from the ultrasound endoscope 2 and is disposed, the movable spring bearing 102 is removed, and the new suction button 10 is attached to the ultrasound endoscope 2 and thus there is no necessity to cleanse the suction button 10. In other words, the suction button 10 is disposable.

The attachment 101 includes an attachment body 1011 that is cylindrical and that is made of rigid resin and an attachment rubber 1012 that is made of an elastic material, such as rubber, silicone or thermoplastic elastomer, and that covers the outer circumference of the attachment body 1011. An attachment fixing part 1012*a* that is claw-shaped is formed on one end of the attachment rubber 1012. The attachment fixing part 1012*a* is engaged with the engagement protrusion 841 of the ferrule 84, so that the attachment 101 is fixed to the ferrule 84. Furthermore, a seal part 1012*b* that makes contact with the ferrule 84 and thus seals the space between the attachment rubber 1012 and the ferrule 84 is formed at an end of the attachment rubber 1012.

The movable spring bearing 102 is joined with the movable piston 105 by ultrasonic welding with part of the attachment 101 and the second coil spring 107 being interposed in between. The movable spring bearing 102 includes a movable spring bearing body 1021 that is cylindrical and that is made of rigid resin and a movable spring bearing packing 1022 that is made of an elastic material, such as rubber, silicone or thermoplastic elastomer, and that covers the outer circumference of the movable spring bearing body 1021. In the movable spring bearing packing 1022, a seal part 1022*a* that slidably seals the space between the attachment body 1011 and the movable spring bearing packing 1022 is formed.

As illustrated in FIG. 9, the shaft 103 extends, forming a shape like a rod. A hole part 1031 that forms a hollow extending in the direction of the center axis Ax1 is formed in the shaft 103. As illustrated in FIG. 7, the hole part 1031 extends from one end of the center axis Ax1 of the shaft 103 and the other end is positioned in the shaft 103. The center axis Ax1 passes through the hole part 1031. In the shaft 103, a communication hole 1031*a* allowing a side surface in a direction orthogonal to the center axis Ax1 and the hole part 1031 to communicate is formed. On an outer circumferential surface of the hole part 1031, a seal part 1031*b* that slidably fits into an inner circumferential surface of the first communication pipe 81*a* and thus seals the space between the first communication pipe 81*a* and the hole part 1031 is formed. The shaft 103 is joined with the cap 104 by ultrasonic welding with part of the movable spring bearing 102 and the first coil spring being interposed in between.

The cap 104 receives an operation of moving the movable spring bearing 102 and the movable piston 105. The cap 104 includes a first member 1041 having a shape of a hollow disk and a second member 1042 that is provided in the first member 1041. The cap 104 is joined with the shaft 103 by ultrasonic welding.

The movable piston 105 is movable such that the movable piston 105 is insertable to the conduit (the third communication conduit 83) of the ultrasound endoscope 2. The movable piston 105 switches between suction conduits of the ultrasound endoscope 2 in response to insertion to or extraction from the conduit (the third communication conduit 83).

The movable piston 105 includes a movable piston body 1051 that is fixed to the movable spring bearing 102, a piston unit 1052 that extends along the conduit (the third communication conduit 83), and a packing 1053 that is arranged around the outer circumference of the piston unit 1052 and that fills the gap between the piston unit 1052 that is inserted into the conduit (the third communication conduit 83) and the conduit (the third communication conduit 83). The movable piston body 1051 and the piston unit 1052 are made of rigid resin that is formed integrally. The piston unit 1052 extends to a position different from the center of the cap 104. The packing 1053 is made of an elastic material, such as rubber, silicone or thermoplastic elastomer, and a seal part 1053*a* that slidably seals the space between the small diameter part 831 of the third communication conduit 83 and the packing 1053 is formed.

The first coil spring 106 is formed by spirally winding a wire rod. The first coil spring 106 is provided between the movable spring bearing 102 and the cap 104 and applies biasing forces to the movable spring bearing 102 and the cap 104 in directions such that the movable spring bearing 102 and the cap 104 separate from each other. The biasing force applied by the first coil spring 106 is received by the surface on which the attachment 101 and the movable piston 105 bump against each other.

The second coil spring 107 is formed by spirally winding a wire rod. The second coil spring 107 is provided between the attachment 101 and the movable spring bearing 102 and applies biasing forces to the attachment 101 and the movable spring bearing 102 in directions such that the attachment 101 and the movable spring bearing 102 separate from each other. In the state where no operation is performed on the suction button 10, part of the attachment 101 makes contact with the movable piston 105 and the first coil spring 106 biases the movable spring bearing 102 and the movable piston 105 such that the movable spring bearing 102 and the movable piston 105 separate from each other. The biasing force applied by the second coil spring 107 is received by the surface on which the attachment 101 and the movable piston 105 bump against each other. The amount of force of the second coil spring 107 of the second coil spring 107 during use is larger than the maximum amount of force of the first coil spring 106 during use.

In the suction button 10, the shaft 103 moves with respect to the movable spring bearing 102 in response to an operation on the cap 104, so that the second communication conduit 821 of the ultrasound endoscope 2 communicates with the first communication conduit 81. In the suction button 10, the movable piston 105 moves integrally with the movable spring bearing 102 with respect to the attachment 101, so that the third communication conduit 83 of the ultrasound endoscope 2 communicates with the second communication conduit 821. More detailed operations of the suction button 10 will be described below.

Assembling the suction button 10 will be described. The movable piston 105 is fitted into the bottom of the attachment 101 (the left side along the center axis Ax1 in FIG. 9). At the fitting, the attachment 101 and the movable piston 105 are fixed to each other such that the attachment 101 and the movable piston 105 do not rotate relatively on Ax1 serving as the rotation axis. Subsequently, the movable spring bearing 102 is attached to the top of the attachment 101 (the right side along the center axis Ax1 in FIG. 9) with the second coil spring 107 interposed in between. At the attachment, the movable spring bearing 102 and the movable piston 105 are fixed by ultrasonic welding.

Thereafter, the shaft 103 is inserted into the bottom of the movable piston 105 that is integrated with the attachment 101, etc. At the insertion, the attachment 101 and the shaft 103 are fixed to each other such that the attachment 101 and the shaft 103 do not rotate relatively with each other on the Ax1 serving as a rotation axis. Subsequently, the cap 104 is attached to the top of the attachment 101 with the first coil spring 106 interposed in between. At the attachment, the shaft 103 and the cap 104 are fixed by ultrasonic welding. In this manner, the above-described suction button 10 is obtained.

Connection conditions of the conduits 6 depending on the air and water supply button 9 and the suction button 10 will be described with reference to FIG. 7 and FIGS. 10 to 15. The case where no operation is performed, the case where a leakage hole 91 of the air and water supply button 9 is sealed with a finger, the case where a first-level pushing operation is performed, the case where a second-level pushing operation is performed will be described sequentially.

Case where No Operation is Performed

Figure 10:
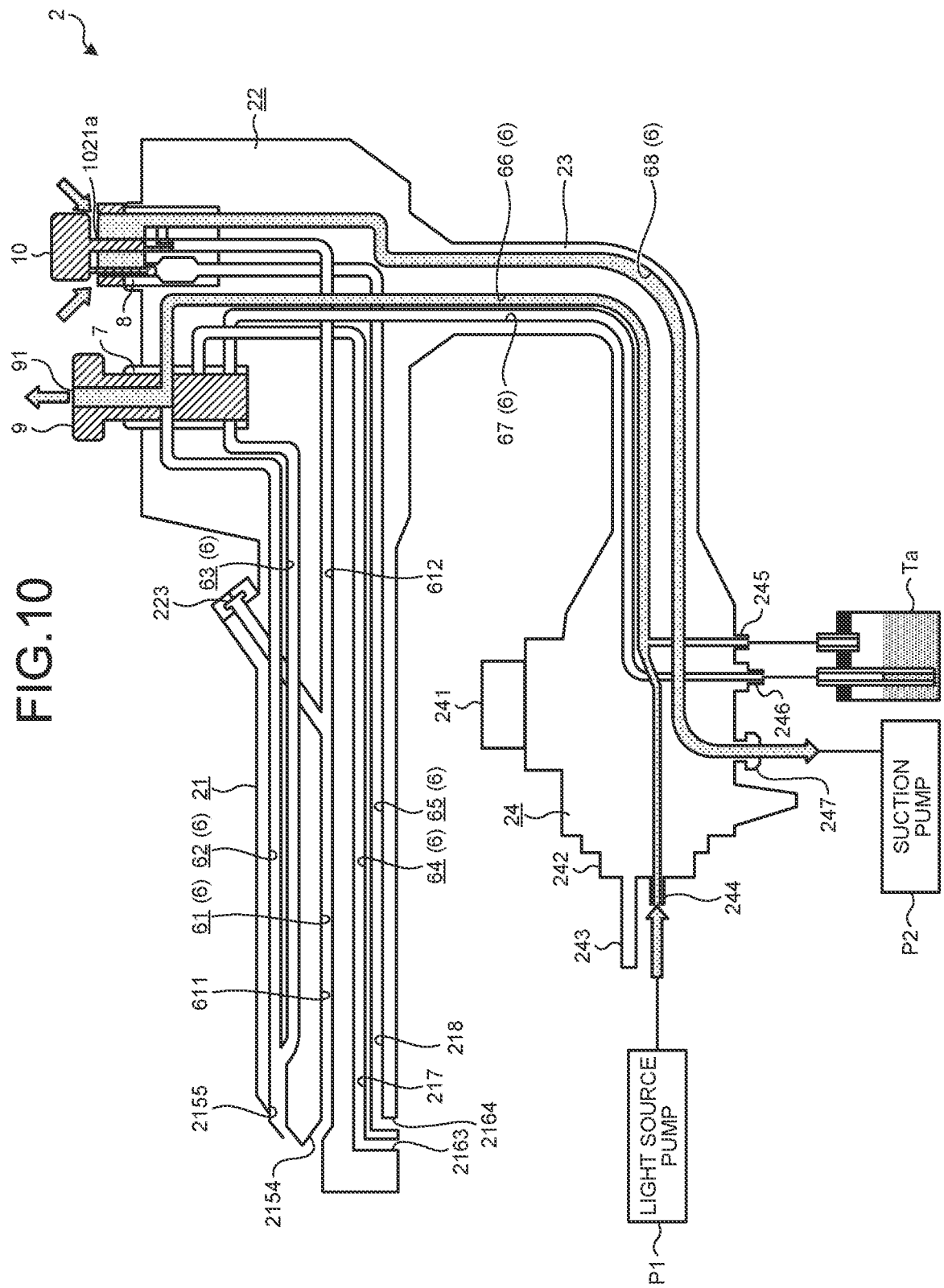
FIG. 10 is a diagram illustrating a connection condition of the conduits in a case where no operation is performed on an air and water supply button and the suction button.

FIGS. 7 and 10 are diagrams illustrating the connection condition of the conduits in the case where no operation is performed on the air and water supply button and the suction button.

In the case where no operation is performed on the air and water supply button 9, the air that is ejected from the light source pump P1 circulates to the air and water supply cylinder 7 via the proximal-end-side first conduit 66. The air having circulated to the air and water supply cylinder 7 passes through the leakage hole 91 and is discharged to the outside of the ultrasound endoscope 2.

In the case where no operation is performed on the suction button 10, the proximal-end-side first conduit 61 is sealed with the seal part 1031*b* and the proximal-end-side fifth conduit 65 is sealed with the seal part 1053*a*. On the other hand, the external air is sealed with the seal parts 1012*b* and 1022*a* and only a leakage hole 1021*a* is open. Thus, in association with driving the suction pump P2, the external air of the ultrasound endoscope 2 flows into the suction cylinder 8 via the leakage hole 1021*a* in the suction button 10 and is sucked by the suction pump P2 via the proximal-end-side third conduit 68. The area of opening of the leakage hole 1021*a* is equal to or larger than the cross-section of the proximal-end-side third conduit 68 and thus the suction pressure caused by the suction pump P2 is prevented from being applied to the distal-end-side first conduit 61 and the distal-end-side fifth conduit 65.

In other words, in the case where no operation is performed, the distal-end-side first to fifth conduits 61 to 65 and the proximal-end-side first to third conduits 66 to 68 are never connected and none of air supply, water supply, and suction is executed from the distal end of the insertion portion 21.

The case where the leakage hole is sealed with a finger

Figure 11:
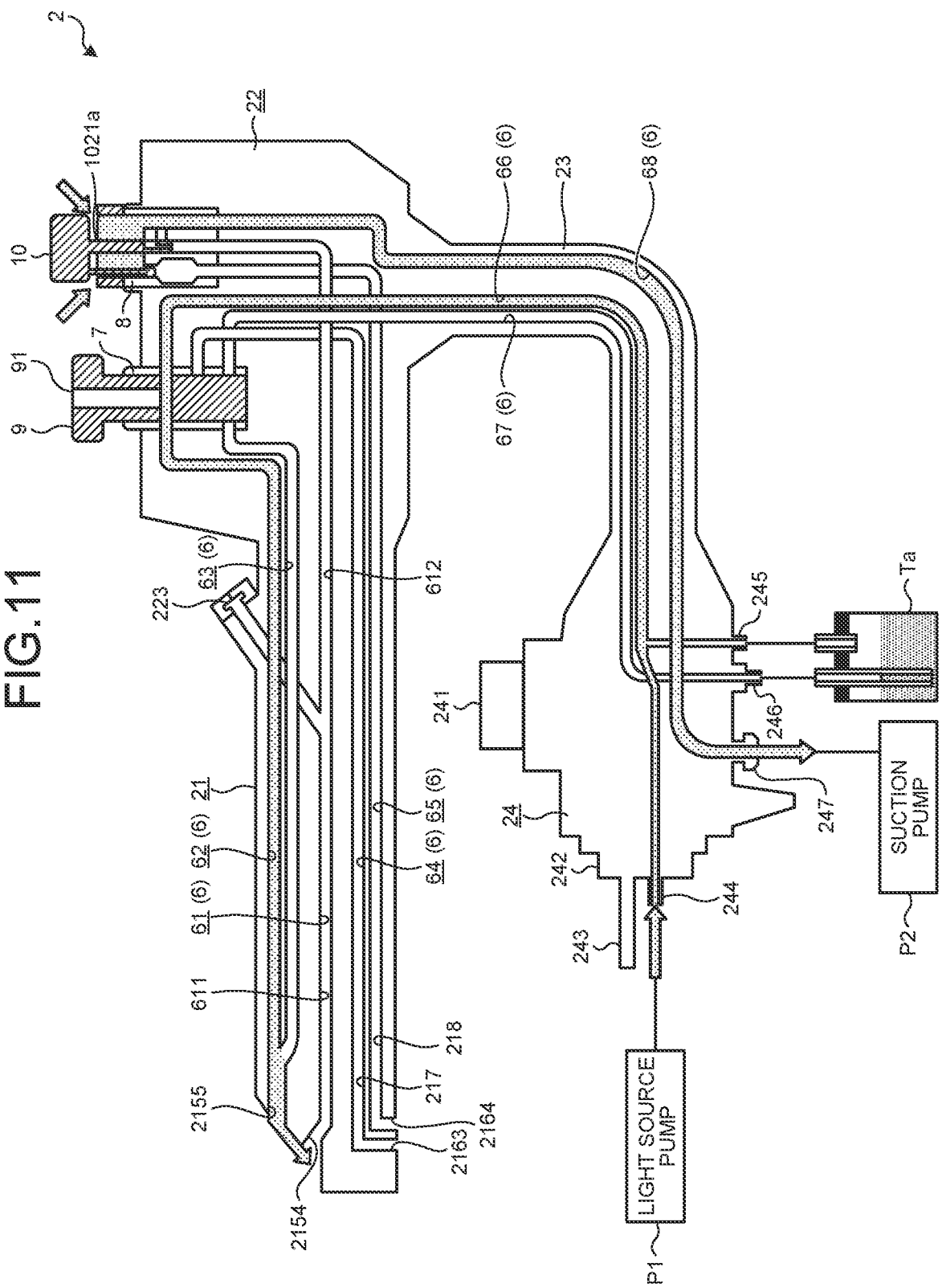
FIG. 11 is a diagram illustrating a connection condition of the conduits in a case where a leakage hole of the air and water supply button is sealed with a finger.

FIG. 11 is a diagram illustrating a connection condition of the conduits in the case where the leakage hole of the air and water supply button is sealed with a finger. Note that, as in FIG. 10, no operation is performed on the suction button 10 in FIG. 11.

When the leakage hole 91 is sealed with a finger, the air that flows into the air and water supply cylinder 7 circulates to the distal-end-side second conduit 62. As illustrated in FIG. 11, the air having circulated to the distal-end-side second conduit 62 is ejected to the objective optical system (not illustrated in the drawing) in the imaging hole (not illustrated in the drawing) from the air and water supply hole 2155.

Case where First-Level Pushing Operation is Performed

Figure 12:
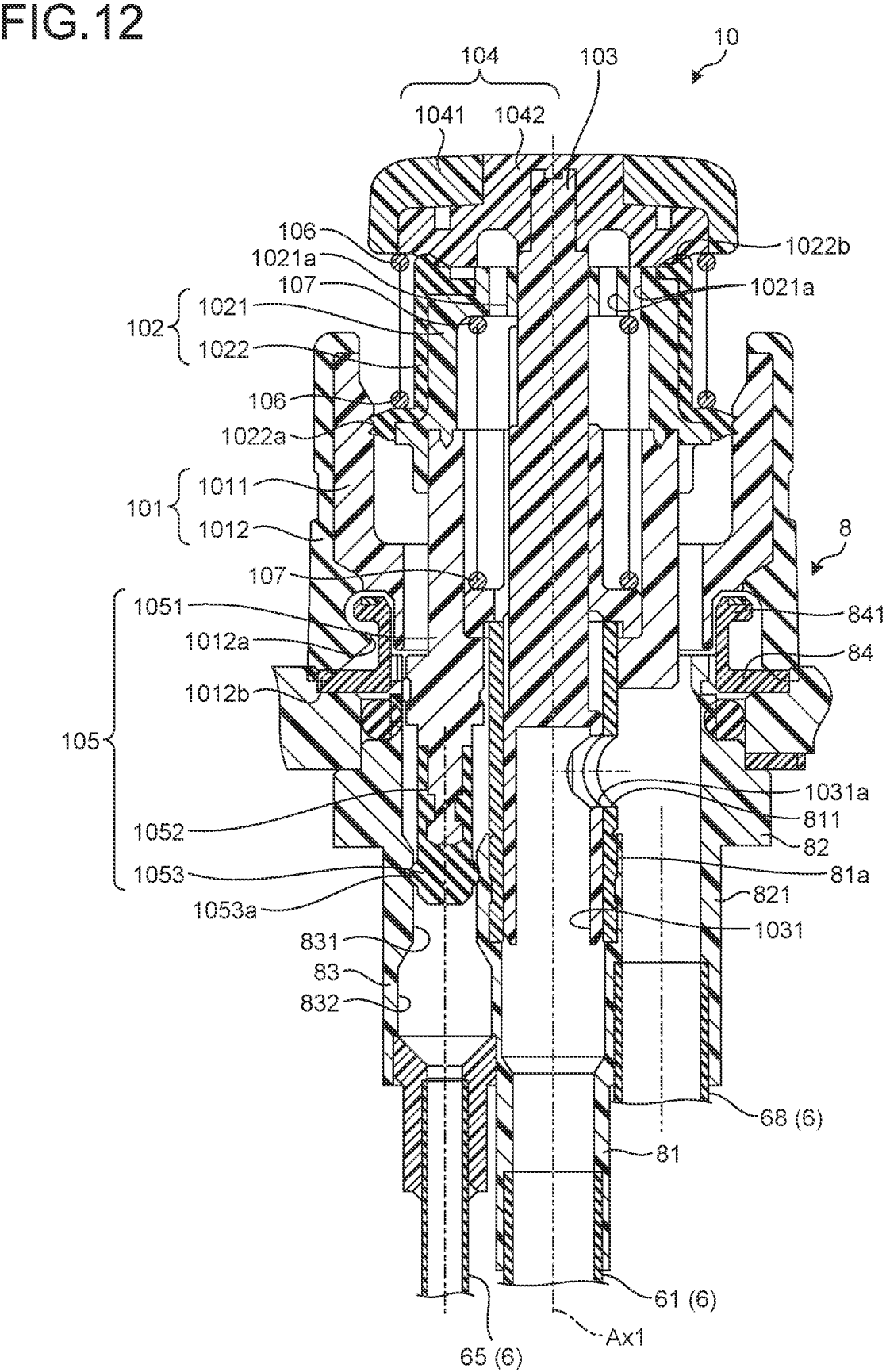
FIG. 12 is a cross-sectional view illustrating a condition at the time when a first-level pushing operation is performed on the suction button.
Figure 13:
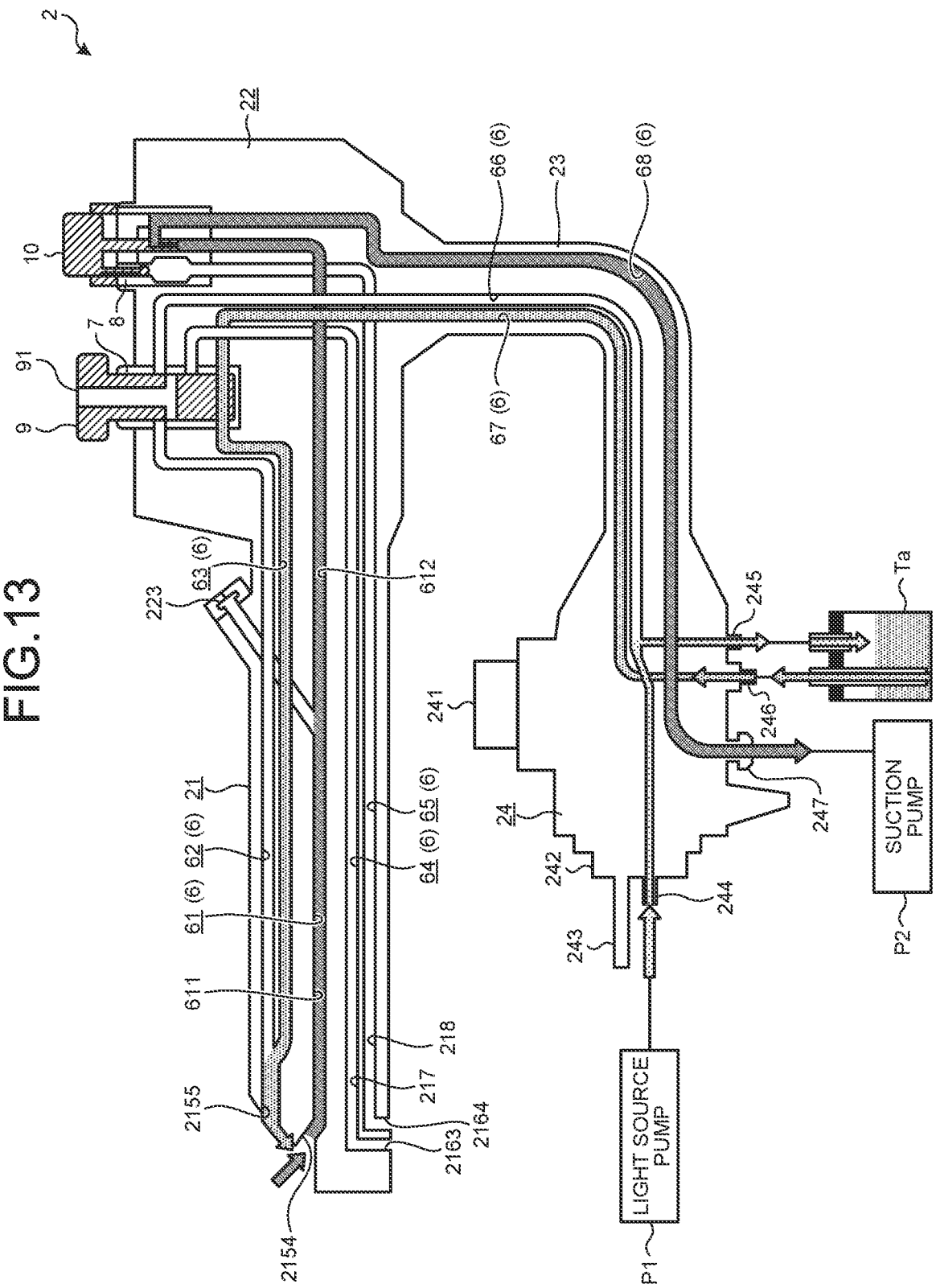
FIG. 13 is a diagram illustrating a connection condition of the conduits in a case where the first-level pushing operation is performed on the air and water supply button and the suction button.

FIG. 12 is a cross-sectional view illustrating a condition at the time when the first-level pushing operation is performed on the suction button. FIG. 13 is a diagram illustrating a connection condition of the conduits in the case where the first-level pushing operation is performed on the air and water supply button and the suction button.

When the first-level pushing operation is performed on the air and water supply button 9, as illustrated in FIG. 13, the air that is ejected from the light source pump P1 flows into the water supply tank Ta via the proximal-end-side first conduit 66, and pressurizes the inside of the water supply tank Ta, thereby causing the water to flow out of the water supply tank Ta. The water from the water supply tank Ta circulates toward the air and water supply cylinder 7 via the proximal-end-side second conduit 67. The water having circulated to the air and water supply cylinder 7 circulates to the distal-end-side third conduit 63. The water having circulated to the distal-end-side third conduit 63 is then ejected from the air and water supply hole 2155 to the objective optical system (not illustrated in the drawing) in the imaging hole (not illustrated in the drawing).

When the first-level pushing operation is performed on the suction button 10, as illustrated in FIG. 12, the cap 104 and the movable spring receiving packing 1022 make contact with each other, so that a seal part 1022b seals the leakage hole 1021a. The shaft 103 that is integrated with the cap 104 by ultrasonic welding slides downward in the first communication pipe 81a, so that the communication hole 1031a is coaxial with the communication hole 811 of the first communication pipe 81a. At the sliding, the distal-end-side fifth conduit 65 is sealed with the seal part 1053a and the external air is sealed with the seal parts 1012b, 1022a and 1022b. On the other hand, the communication-hole 1031a of the shaft 103 and the communication hole 811 of the first communication pipe 81a are made coaxial with each other (open), so that the distal-end-side first conduit 61 and the proximal-end-side third conduit 68 are connected (communicate). The liquid in the subject flows into the distal-end-side first conduit 61 from the instrument channel 2154 and is sucked by the suction pump P2 via the suction cylinder 8 and the proximal-end-side third conduit 68. Note that a forceps clamp (not illustrated in the drawing) is attached to the treatment instrument channel insertion port 223 in order to clog the treatment instrument channel insertion port 223 to apply the suction pressure to the distal end side (the side of the instrument channel 2154) when liquid in the subject is sucked from the instrument channel 2154 as described above.

Case where Second-Level Pushing Operation is Performed

Figure 14:
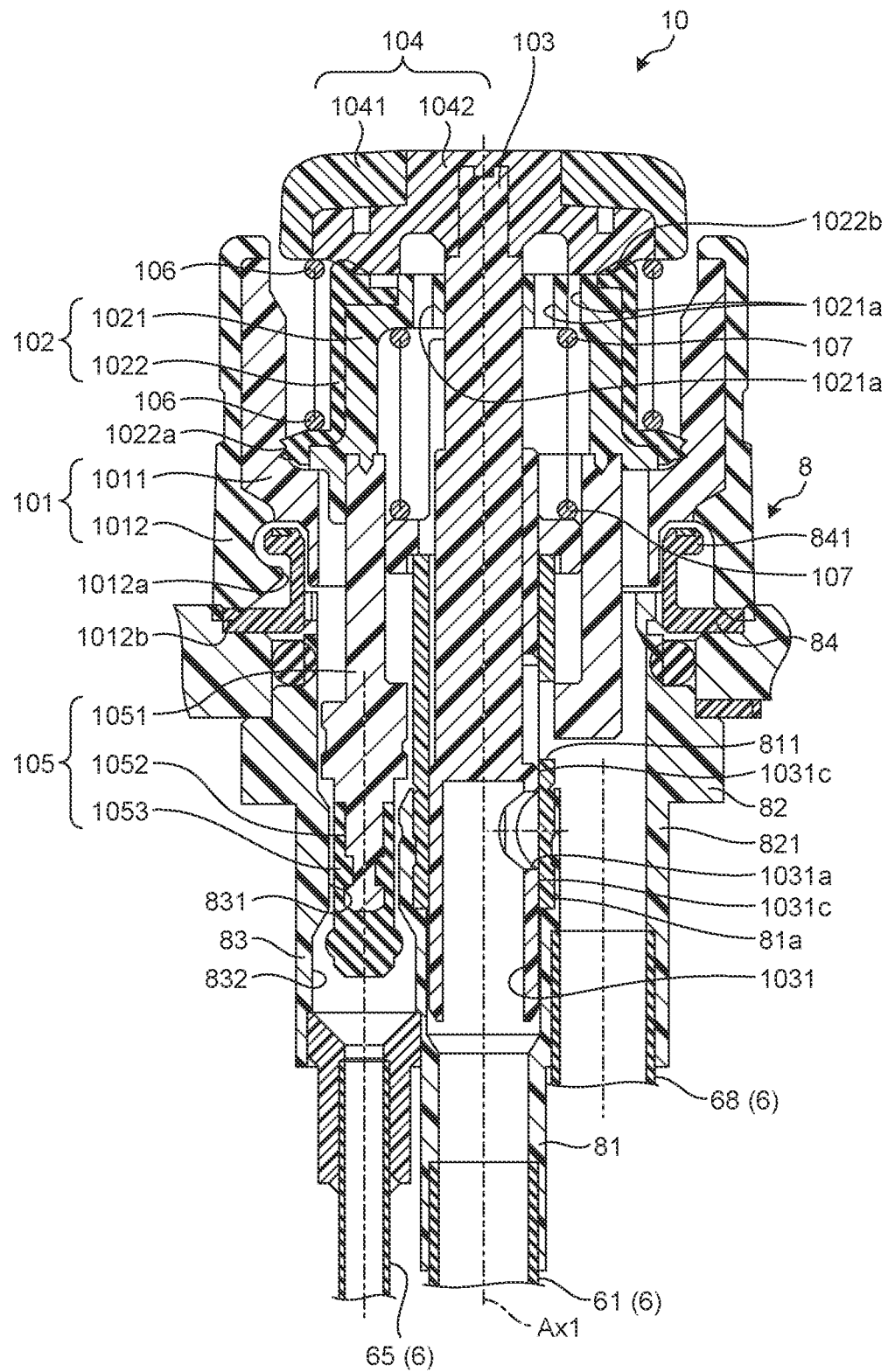
FIG. 14 is a cross-sectional view illustrating a condition at the time when a second-level pushing operation is performed on the suction button.

FIG. 14 is a cross-sectional view illustrating a condition at the time when the second-level pushing operation is performed on the suction button. FIG. 15 is a diagram illustrating a connection condition of the conduits in the case where the second-level pushing operation is performed on the air and water supply button and the suction button.

When the second-level pushing operation is performed on the air and water supply button 9 (the first-level pushing operation is further performed in the condition illustrated in FIG. 13), the water having circulated to the air and water supply cylinder 7 circulates to the distal-end-side fourth conduit 64. As illustrated in FIG. 15, the water having circulated to the distal-end-side fourth conduit 64 is supplied into the balloon (not illustrated in the drawing) via the water supply hole 217 and the balloon filling port 2163.

When the second-level pushing operation is performed on the suction button 10, as illustrated in FIG. 14, with the sealing between the cap 104 and the movable spring bearing 102 with the seal part 1022b and the sealing between the movable spring bearing 102 and the attachment 101 with the seal part 1022a being maintained, the shaft 103 and the movable piston 105 respectively move downward through the first communication pipe 81a and the third communication conduit 83 and the shaft 103 is slidably fitted into the first communication pipe 81a and thus a seal part 1031c seals the space between the shaft 103 and the first communication pipe 81a and the packing 1053 of the movable piston 105 is positioned in the large-diameter part 832 from the small diameter part 831 of the third communication conduit 83. At the second-level pushing operation, the distal-end-side first conduit 61 is sealed with the seal part 1031c and the external air is sealed with the seal parts 1012b, 1022a and 1022b. On the other hand, the packing 1053 of the movable piston 105 moves to the large diameter part 832 of the third communication conduit 83 and thus the seal part 1053a is open and the distal-end-side fifth conduit 65 and the proximal-end-side third conduit 68 are connected (communicate). The liquid (for example, water in the balloon) in the subject flows into the distal-end-side fifth conduit 65 from the balloon suction port 2164 and is sucked by the suction pump P2 via the suction cylinder 8 and the proximal-end-side third conduit 68.

The joint between the movable spring bearing 102 and the movable piston 105 will be described. FIGS. 16A and 16B are a partial enlarged view of Area B in FIG. 7 and FIG. 16A illustrates the joint before welding and FIG. 16B illustrates the joint after welding. As illustrated in FIGS. 16A and 16B, the movable spring bearing body 1021 of the movable spring bearing 102 includes a rib 1021b that is cylindrical. The movable piston body 1051 of the movable piston 105 has a rib receiver groove 1051a into which the rib 1021b is inserted. The movable spring bearing 102 and the movable piston 105 are joined by ultrasonic welding. As a result, a welded part end 1021c of the rib 1021b and a polarization surface part of a bottom surface 1051b of the rib receiver groove 1051a are joined and accordingly a welded part (welded surface) 10a is formed. A gap is formed between a side surface of the rib 1021b and a side surface of the rib receiver groove 1051a and a welded resin 1021d of the rib 1021b flows into at least part of the gap and is supplied as the resin 10b, which reinforces the joint between the movable spring bearing 102 and the movable piston 105 as an adhesive does. The resin 10b serves as a force in a shear direction against a force in a tensile direction of the movable spring bearing 102 against the movable piston 105 and thus the adhesion strength increases. As a result, according to the embodiment, it is possible to prevent the movable spring bearing 102 and the movable piston 105 that are made of resin from separating from each other. It is preferable that the welded resin 10b whose volume is at or above 50% of the volume of the gap between the side surface of the rib 1021b and the side surface of the rib receiver groove 1051a be supplied to the gap. This is because, the higher the ratio of the supplied resin to the gap increases, the more the joint between the movable spring bearing 102 and the movable piston 105 becomes stronger.

The above-described endoscope disposable conduit switching device (the suction button 10) according to the embodiment employs the configuration for switching the connection condition of the conduits 6 by performing the pushing operations at two levels. Alternatively, a configuration in which only a pushing operation at a single level is executable may be employed.

In the above-described embodiment, the endoscope system 1 has been described as one having both a function of generating an ultrasound image and a function of generating an endoscopic image. Alternatively, a configuration with only the function of generating an ultrasound image may be employed.

In the above-described embodiment, the endoscope system 1 is not limited to the field of medicine and the endoscope system 1 may be an endoscope system that internally observers a subject, such as a mechanical structure, in the field of industry.

According to the disclosure, it is possible to realize an endoscope disposable conduit switching device that prevents a movable spring bearing made of resin and a movable piston from separating from each other.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope conduit switching device comprising:
   an attachment body extending in a longitudinal direction, the attachment body configured to be attached to an endoscope;
   a shaft inserted into the attachment body, the shaft extending in the longitudinal direction;
   a cap fixed to one end of the shaft;
   a piston movably disposed relative to each of the attachment body and the shaft, the piston comprising:
      a first piston portion having a rib; and
      a second piston portion having a rib receiver groove into which the rib is inserted; and
   an elastic material configured to bias the piston and the cap away from each other in the longitudinal direction,
   wherein the rib is fixed in the rib receiver groove by adhering at least a portion of the rib to a corresponding portion of the rib receiving groove.

2. The endoscope conduit switching device according to claim 1, wherein the attachment body is detachably attached to the endoscope.

3. The endoscope conduit switching device according to claim 1, wherein
   the rib is at least partially provided along a circumferential direction of the shaft, and
   the rib receiver groove is provided along the circumferential direction of the shaft.

4. The endoscope conduit switching device according to claim 1, wherein a side surface of the rib and a side surface of the rib receiver groove are at least partially fixed with each other.

5. The endoscope conduit switching device according to claim 1, wherein the rib extending in the longitudinal direction.

6. An endoscope comprising:
   an endoscope body including an insertion portion configured to be inserted into a subject and an operation portion provided on a proximal end side of the insertion portion; and
   the endoscope conduit switching device according to claim 1, provided in the operation portion of the endoscope body.

7. The endoscope according to claim 6, wherein the endoscope body is an ultrasound endoscope including an ultrasound probe in the insertion portion.

8. The endoscope conduit switching device according to claim 1, wherein
   the first piston portion is formed of resin, and
   the second piston portion is formed of resin.

9. The endoscope conduit switching device according to claim 8, wherein the elastic material comprises a first elastic material and the endoscope conduit switching device further comprising a second elastic material configured to bias the attachment body and the piston away from each other.

10. The endoscope conduit switching device according to claim 8, wherein the piston is configured to switch between suction conduits of the endoscope.

11. The endoscope conduit switching device according to claim 8, wherein
   the shaft is configured to move with respect to each of the piston and the attachment body to establish a first fluid flow through the endoscope, and
   the piston and the shaft are configured to move together with respect to the attachment body to establish a second fluid flow, different from the first fluid flow, through the endoscope.

12. The endoscope conduit switching device according to claim 8, wherein the endoscope conduit switching device is a disposable component.

13. The endoscope conduit switching device according to claim 8, wherein
   the piston comprises a welded part where a distal end of the rib and a bottom surface of the rib receiver groove are welded and fixed with each other, and
   welded resin is filled into at least part of a gap between a side surface of the rib and a side surface of the rib receiver groove.

14. The endoscope conduit switching device according to claim 13, wherein the welded resin is filled with at least 50% of a volume of the gap.

\* \* \* \* \*